(12) United States Patent
Witte et al.

(10) Patent No.: US 9,592,309 B2
(45) Date of Patent: Mar. 14, 2017

(54) POSITRON EMISSION TOMOGRAPHY PROBE TO MONITOR SELECTED SUGAR METABOLISM IN VIVO

(71) Applicant: The Regents of the University of California, Oakland, CA (US)

(72) Inventors: Owen Witte, Sherman Oaks, CA (US); Peter M. Clark, Los Angeles, CA (US); Blanca Graciela Flores Castillo, Van Nuys, CA (US); Michael E. Jung, Los Angeles, CA (US); Nikolai M. Evdokimov, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 56 days.

(21) Appl. No.: 14/399,701

(22) PCT Filed: May 9, 2013

(86) PCT No.: PCT/US2013/040425
§ 371 (c)(1),
(2) Date: Nov. 7, 2014

(87) PCT Pub. No.: WO2013/170085
PCT Pub. Date: Nov. 14, 2013

(65) Prior Publication Data
US 2015/0133777 A1    May 14, 2015

Related U.S. Application Data

(60) Provisional application No. 61/644,660, filed on May 9, 2012, provisional application No. 61/761,350, filed on Feb. 6, 2013.

(51) Int. Cl.
| | | |
|---|---|---|
| *A61K 51/00* | (2006.01) |
| *A61M 36/14* | (2006.01) |
| *A61K 51/04* | (2006.01) |
| *A61K 49/04* | (2006.01) |
| *A61B 6/03* | (2006.01) |
| *A61B 6/00* | (2006.01) |
| *C07H 1/00* | (2006.01) |
| *C07H 5/02* | (2006.01) |
| *G21G 1/00* | (2006.01) |

(52) U.S. Cl.
CPC .......... *A61K 51/0491* (2013.01); *A61B 6/032* (2013.01); *A61B 6/037* (2013.01); *A61B 6/507* (2013.01); *A61K 49/0433* (2013.01); *C07H 1/00* (2013.01); *C07H 5/02* (2013.01); *G21G 1/0005* (2013.01); *C07B 2200/05* (2013.01)

(58) Field of Classification Search
CPC    A61K 51/0491; A61K 49/0433; A61B 6/032; A61B 6/037; A61B 6/507; C07B 2200/05; C07H 1/00; C07H 5/02; G21G 1/0005
USPC ........................................................ 424/1.89
See application file for complete search history.

(56) References Cited

FOREIGN PATENT DOCUMENTS

| | | |
|---|---|---|
| WO | WO 2004096138 A2 * | 11/2004 |
| WO | 2006-127842 | 11/2006 |
| WO | 2009-038795 | 3/2009 |

OTHER PUBLICATIONS

Park et al. FEBS Lett. 581 (2007) 3211-3216.*
Deng et al. Chem. Commun., 2006, 652-654.*
Waldherr et al. J Nucl. Med. 2005, 46, 114-120.*
Mashhedi et al. Cell Cycle 2011, 10, 2770-2778.*
Goncalves et al. Anat. Rec. 1969, 165, 543-558.*
Dittman et al. (Eur. J Nucl. Med. (2002) 29: 1562-1469.*
Alauddin, M.M. et al. "Synthesis of 2'-deoxy-2'-fluoro-1-B-D-arabinofuranosyl uracil derivatives: a method suitable for preparation of [18F]-labeled nucleosides", Synthetic Communications, 2002, vol. 32, No. 11, pp. 1757-1764.
Buriova, E. et al. "Autoradiolysis of the 2-deoxy-2-[18F]fluoro-D-glucose radiopharmaceutical", Journal of Radioanalytical and Nuclear Chemistry, 2005, vol. 264, No. 3, pp. 595-602.
Alauddin, M.M. et al. "Biodistribution and PET imaging of [18F]-fluroadenosine derivatives", Nuclear Medicine and Biology, 2007, vol. 34, pp. 267-272.
PCT International Search Report and Written Opinion dated Aug. 21, 2013 for PCT Application No. PCT/US2013/040425.

* cited by examiner

*Primary Examiner* — Michael G Hartley
*Assistant Examiner* — Sean R Donohue
(74) *Attorney, Agent, or Firm* — Gates & Cooper, LLP

(57) ABSTRACT

The invention disclosed herein discloses selected ribose isomers that are useful as PET probes (e.g. [18F]-2-fluoro-2-deoxy-arabinose). These PET probes are useful, for example, in methods designed to monitor physiological processes including ribose metabolism and/or to selectively observe certain tissue/organs in vivo. The invention disclosed herein further provides methods for making and using such probes.

17 Claims, 16 Drawing Sheets

POSITRON EMISSION TOMOGRAPHY PROBE TO MONITOR SELECTED SUGAR METABOLISM IN VIVO

CROSS-REFERENCE TO RELATED APPLICATIONS

This application claims the benefit under 35 U.S.C. Section 119(e) of U.S. Provisional Patent Application Ser. No. 61/644,660 filed May 9, 2012, and U.S. Provisional Patent Application Ser. No. 61/761,350 filed Feb. 6, 2013 both entitled "A POSITRON EMISSION TOMOGRAPHY PROBE TO MONITOR SELECTED SUGAR METABOLISM IN VIVO" the contents of each which are incorporated herein by reference.

STATEMENT AS TO RIGHTS TO INVENTIONS MADE UNDER FEDERALLY SPONSORED RESEARCH AND DEVELOPMENT

This invention was made with Government support under Grant Number DE-SC0001249, awarded by the U.S. Department of Energy and under Grant Number CA098010, awarded by the National Institutes of Health. The Government has certain rights in the invention.

TECHNICAL FIELD

The present disclosure relates to tomography probes useful as selective imaging agents.

BACKGROUND OF THE INVENTION

Positron emission tomography (PET) is a medical imaging technique that is commonly used to produce three-dimensional images in vivo. This technique detects gamma rays emitted by a positron-emitting radionuclide tracer that has been administered to a subject. Three-dimensional images of tracer concentrations within the subject's body can then be constructed by computer analysis. In this way, PET can be used, for example, to observe a variety of organs and/or physiological processes such as cellular metabolism and protein synthesis, as well as well as pathological conditions such as cancer and heart disease.

$^{18}$F-Fluoro-2-Deoxy-D-glucose ($^{18}$F-FDG) is a common clinical PET probe that is used, for example, to diagnose certain pathological conditions including cancer as well as to evaluate the effects of certain therapeutic regimens. $^{18}$F-FDG however, has high absorption ratios in certain tissues such as the brain, heart, kidney and bladder. For this reason, background signals can be a problem when using this molecule at a probe. In addition, some tissues of primary liver cancer and clear cell renal cell carcinoma (CCRCC) do not selectively absorb $^{18}$F-FDG, a phenomena that can lead to false negatives. $^{18}$F-FDG also has high absorption ratios in inflamed areas, another characteristic which can contribute to erroneous diagnoses. These characteristics of $^{18}$F-FDG's limit its applications in vivo.

Compounds useful as probes in positron emission tomography can contain [18F]-2-fluoro-2-deoxyarabinose ([18F]-FDA) as part of the molecule, such as 1-(2'-deoxy-2'-[$^{18}$F]fluoro-β-D-arabinofuranosyl)cytosine (see, e.g. Radu et al. *Nat Med.* 2008 July; 14(7):783-8), 1-(2'-deoxy-2'-[$^{18}$F]fluoro-β-D-arabinofuranosyl)-5-methylcytosine (see, e.g. Shu C J, et. al. *J Nucl Med.* 2010 July; 51(7):1092-8), and 2'-deoxy-2'-[$^{18}$F]fluoro-9-β-D-arabinofuranosylguanine (see, e.g. Namavari M, et al. *Mol Imaging Biol.* 2011 October; 13(5):812-8). However, it has not been determined if any discrete [$^{18}$F]-FDA compound alone possesses a pharmacokinetic profile that allows it to be used as a PET probe in vivo, much less if a [$^{18}$F]-FDA compound may be useful to monitor specific physiological processes in vivo.

SUMMARY OF THE INVENTION

The invention disclosed herein provides compounds that are useful as probes in processes such as positron emission tomography, as well as methods for making and using them. Embodiments of the invention include methods for using the PET probes to observe specific organs and tumor subtypes, as well certain metabolic disorders in mammals. The working embodiments of the invention that are disclosed herein demonstrate how these probes can be used to monitor liver function in vivo, in order to, for example, identify areas of abnormal activity in the liver (including the presence of primary and secondary neoplastic lesions), and/or to observe liver dysfunction, and/or to observe liver regeneration.

The invention disclosed herein has a number of embodiments. One embodiment of the invention is a composition of matter comprising a positron emission tomography probe selected from the group consisting of $^{18}$F labelled: 2-fluoro-2-deoxyarabinose; 3-fluoro-3-deoxyarabinose; 2-fluoro-2-deoxyribose; 3-fluoro-3-deoxyribose; 1-fluoro-1-deoxy-alpha-ribose; and 1-fluoro-1-deoxy-beta-ribose. As discussed in detail below, it has been discovered that when these PET probes are administered to a subject, they selectively accumulate in certain tissues, a phenomena that can be observed via a process such as positron emission tomography. In illustrative embodiments of the invention that are disclosed herein, a $^{18}$F labelled 2-fluoro-2-deoxyarabinose PET probe is shown to selectively accumulate in murine liver, kidney and intestinal tissues.

Embodiments of the invention include methods of observing cellular metabolism in vivo in a mammal using the PET probes disclosed herein. These methods typically comprise the steps of administering a composition to the mammal comprising a positron emission tomography probe selected from the group consisting of $^{18}$F labelled 2-fluoro-2-deoxyarabinose, 3-fluoro-3-deoxyarabinose, 2-fluoro-2-deoxyribose, 3-fluoro-3-deoxyribose, 1-fluoro-1-deoxy-alpha-ribose or 1-fluoro-1-deoxy-beta-ribose and then allowing the probe to accumulate in cells/tissues of the mammal The cells/tissues having this accumulated probe can then be observed using a positron emission tomography and/or computed tomography (CT) process.

Embodiments of the invention use the disclosed PET probes to observe metabolic phenomena that are characteristic of certain biological processes. For example, in some embodiments of the invention a PET probe is used to examine cells for metabolic phenomena that are observed in disease syndromes such as cancer or diabetes. In other embodiments of the invention a PET probe is used to examine cells for metabolic phenomena that are observed in cells responding to a therapeutic agent such an anti-cancer agent or anti-diabetic agent administered to the mammal In illustrative embodiments of the invention, a PET probe is used to examine cells for metabolic phenomena that are observed in cells responding to an oxythiamine, insulin, metformin, leflunomide or a methotrexate composition. In one specific illustrative embodiment of the invention, the mammal is a human, the PET probe consists of 2-fluoro-2-deoxyarabinose:

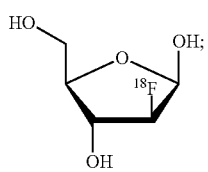

and cellular metabolism in liver, kidney, and/or intestinal tissues is selectively observed using a positron emission tomography process.

Related embodiments of the invention include methods of selectively observing an in vivo tissue or organ in a mammal such as liver, kidney, and/or intestinal tissues. Such methods comprise the steps of administering a composition to the mammal that includes a positron emission tomography probe selected from the group consisting of $^{18}F$ labelled 2-fluoro-2-deoxyarabinose, 3-fluoro-3-deoxyarabinose, 2-fluoro-2-deoxyribose, 3-fluoro-3-deoxyribose, 1-fluoro-1-deoxy-alpha-ribose, and 1-fluoro-1-deoxy-beta-ribose. Typically in these methods, the positron emission tomography probe is administered to the mammal in combination with a pharmaceutically acceptable compound comprising a diluent, a carrier, or a binding agent. Following this administration, the probe is then allowed to selectively accumulate in a tissue or organ such as liver, kidney, and/or intestinal tissues. The probe in the mammal can then be used to observe an in vivo tissue or organ where it has accumulated, typically by using a positron emission tomography and/or a computed tomography process. In this way, a mammalian tissue or organ such as liver, kidney, and/or intestinal tissues can selectively observed in vivo.

Embodiments of the invention use the disclosed PET probes to observe metabolic phenomena that are characteristic of certain biological processes such as the cellular metabolism of liver, kidney, and/or intestinal tissue. For example, some embodiments of observed cellular metabolism in such a tissue to detect the presence or absence of metabolic phenomena that are characteristic of a metabolic disorder, tumor growth, gluconeogenesis, a neurodegenerative syndrome, a syndrome characterized by ischemia, a syndrome characterized by chronic inflammation, congestive heart failure, stroke or the like. Similar embodiments of the invention include methods for observing a physiological activity in the liver that is observed in liver dysfunction, liver cancer or liver regeneration.

Other embodiments of the invention include methods of synthesizing PET probes such as [$^{18}F$]-2-fluoro-2-deoxyarabinose. As discussed in detail below, in one embodiment of the invention, this method comprises synthesizing [$^{18}F$]-2-fluoro-2-deoxy-arabinose by producing [$^{18}F$]-fluoride ion by bombarding enriched [$^{18}O$] water, treating the [$^{18}F$]-fluoride ion with $K_2CO_3$ and 4,7,13,16,21,24-Hexaoxa-1,10-diazabicyclo[8.8.8]-hexacosane so as to form a first mixture, performing azeotropic distillation on the first mixture, adding 2-O-(trifluoromethylsulfonyl)-1,3,5-tri-O-benzoyl-alpha-D-ribofuranose to the first mixture, loading the first mixture onto a silica matrix, eluting [18F]-2-fluoro-2-deoxy-1,3,5-tri-O-benzoyl-alpha-ribofuranose from the matrix with ethyl acetate; and then adding sodium methoxide to the [$^{18}F$]-2-fluoro-2-deoxy-1,3,5-tri-O-benzoyl-alpha-ribofuranose to form a second mixture, wherein the second mixture forms [$^{18}F$]-2-fluoro-2-deoxy-arabinose. Typically these methods comprise loading the second mixture onto a chromatographic column system; and then eluting the [18F]-FDA with water.

Other embodiments of the invention include kits, for example, those including a plurality of containers that hold one or more reagents useful in a PET process. In one illustrative embodiment, the kit includes one or more compounds selected from the group consisting of 2-fluoro-2-deoxyarabinose, 3-fluoro-3-deoxyarabinose, 2-fluoro-2-deoxyribose, 3-fluoro-3-deoxyribose, 1-fluoro-1-deoxy-alpha-ribose or 1-fluoro-1-deoxy-beta-ribose as well as articles or materials useful to label the compound with $^{18}F$ (e.g. an article or material disclosed in Example 1 below). In some embodiments of the invention, the kit includes articles useful to administer the probe, for example a capsule that can surround the probe (e.g. for use when the probe is administered orally) or a needle and syringe (e.g. for use when the probe is administered parenterally).

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE INVENTION

Unless otherwise defined, all terms of art, notations and other scientific terms or terminology used herein are intended to have the meanings commonly understood by those of skill in the art to which this invention pertains. Many of the techniques and procedures described or referenced herein are well understood and commonly employed using conventional methodology by those skilled in the art. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification. In the description of the preferred embodiment, reference is made to the accompanying drawings which form a part hereof, and which is shown by way of illustration a specific embodiment in which the invention may be practiced. It is to be understood that other embodiments may be utilized and structural changes may be made without departing from the scope of the present invention.

Figure 1:
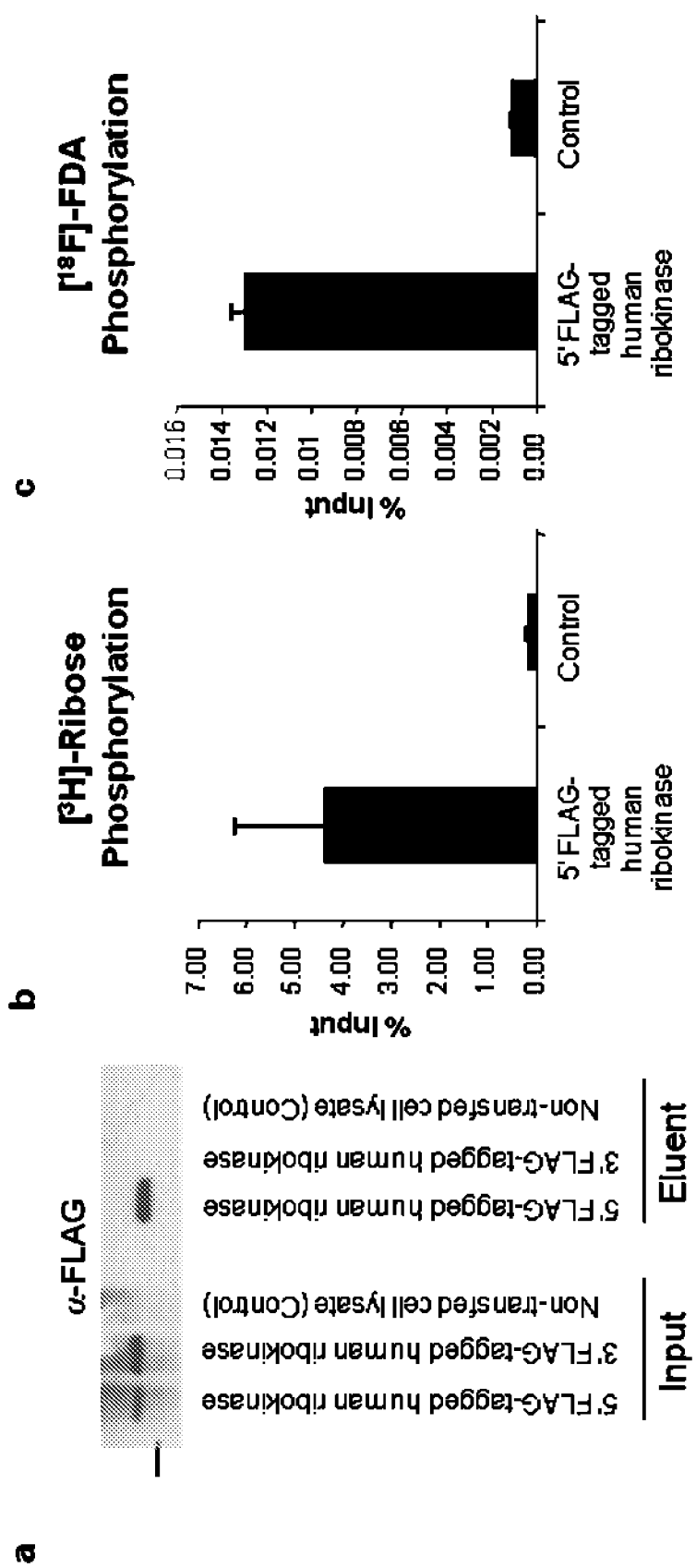
FIG. 1 provides data showing isolated 5' FLAG-tagged human ribokinase phosphorylates [$^3H$]-Ribose and [$^{18}F$]-FDA. (a) Western Blot showing FLAG-tagged human ribokinase expressed and isolated from 293T cells. (b,c) Bar graphs of data from kinase reactions containing [$^3H$]-Ribose (b) and [$^{18}F$]-FDA (c).
Figure 2:
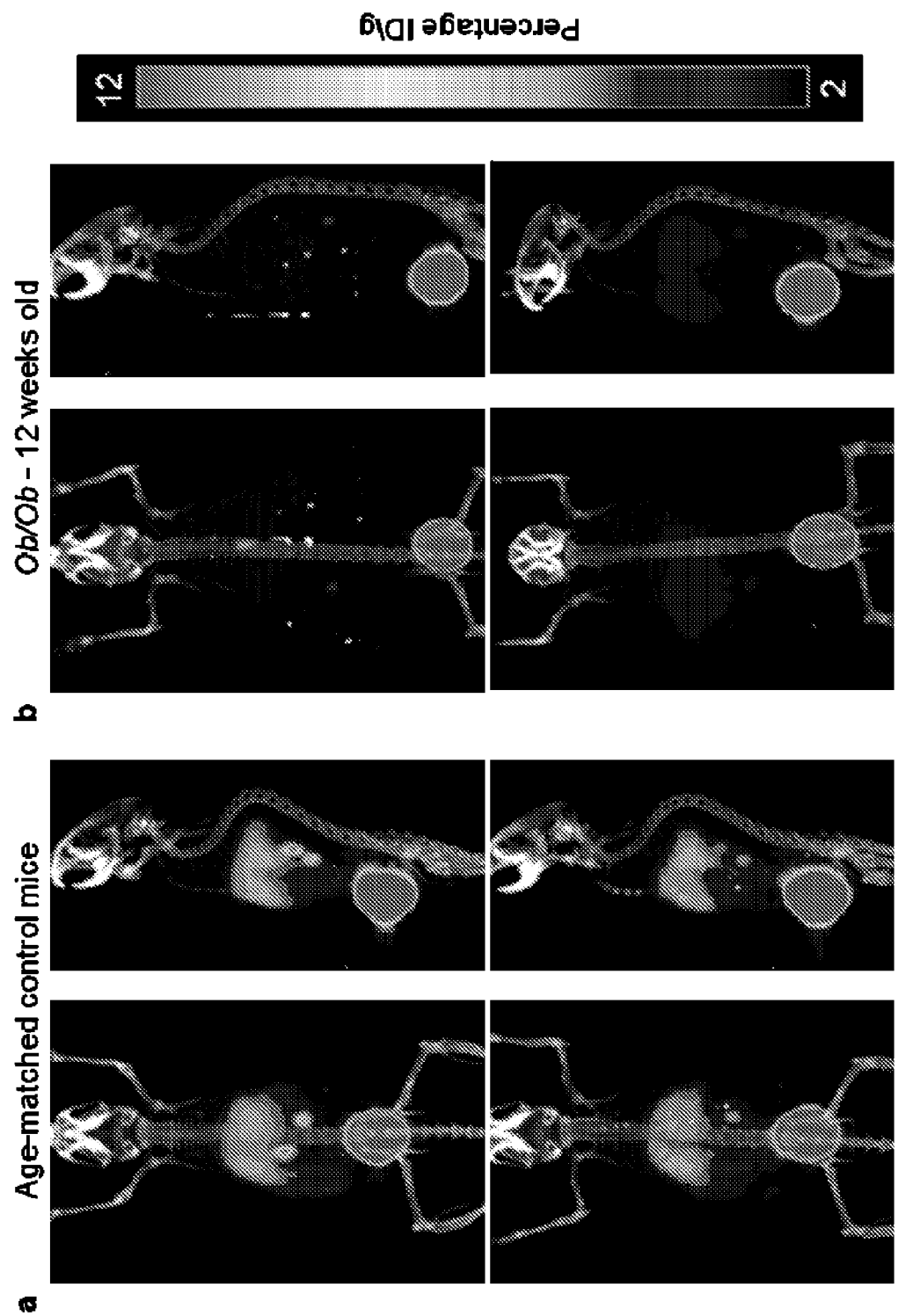
FIG. 2 provides data showing [$^{18}F$]-FDA localizing significantly to the liver of wild-type but not Ob/Ob mice. (a) 12 week old C57B1/6 female mice and (b) Ob/Ob mice were treated with [$^{18}F$]-FDA for 1 hour and imaged with positron emission tomography (PET) followed by computed tomography (CT) imaging.
Figure 3:
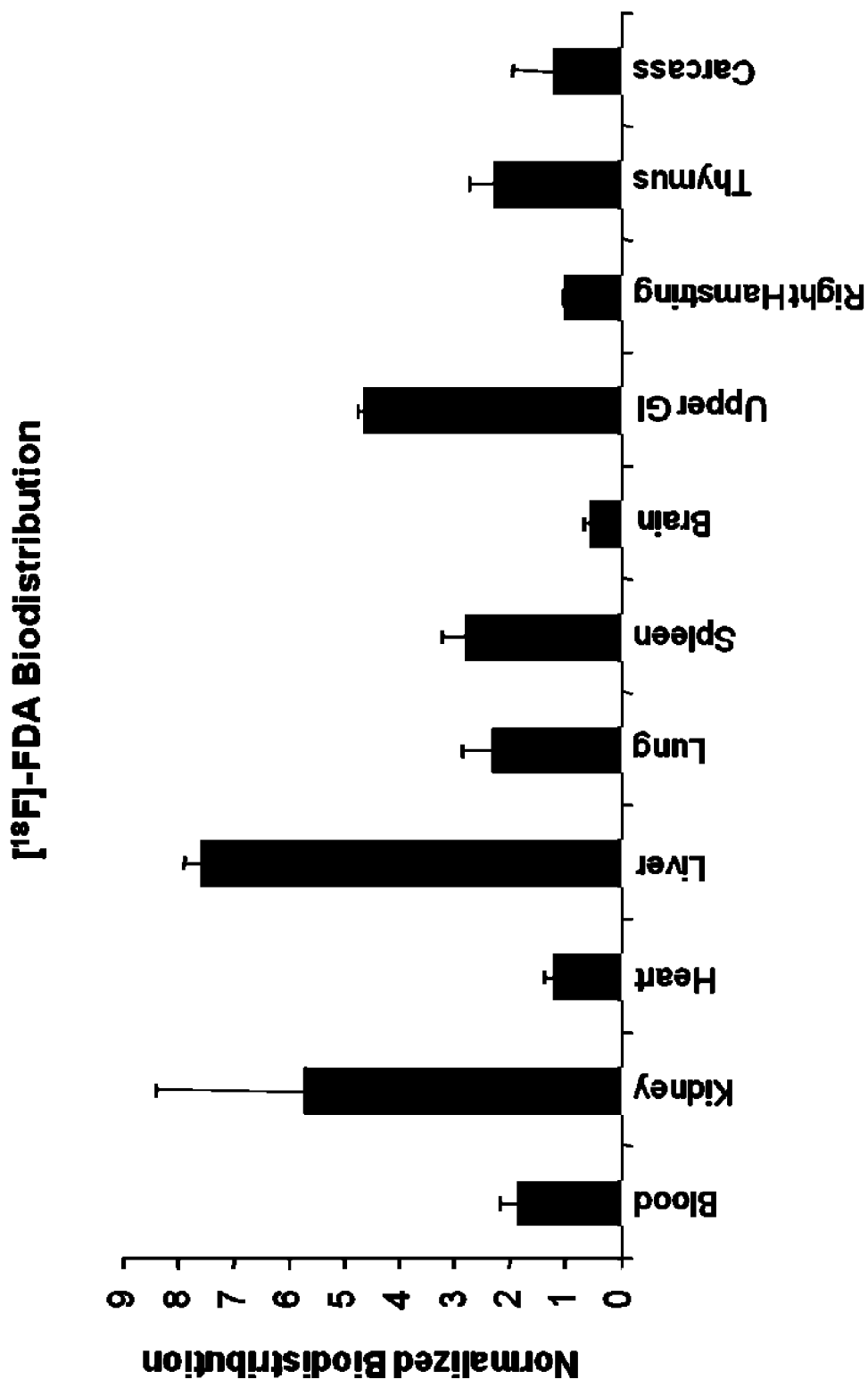
FIG. 3 provides a graph of data showing [$^{18}F$]-FDA biodistribution following 1.5 hour uptake in C57B1/6 female mice.

The invention disclosed herein provides ribose compounds having properties that make them useful as PET probes, for example, to monitor ribose metabolism in vivo. The data presented herein demonstrates that compounds including [$^{18}$F]-2-fluoro-2-deoxyarabinose very specifically localize to certain tissues that express ribokinase, such as the liver. The data presented herein further illustrates the usefulness of these PET probes by demonstrating that [$^{18}$F]-FDA uptake in the liver is dependent on the metabolic status of the mouse, with leptin knockout mice (a mouse model of type 2 diabetes) showing a severe deficit in uptake of the probe compared with wild-type mice (FIG. 2). Ribose is an intermediate in the pentose phosphate pathway, where it can be metabolized through gluconeogenic pathways to glucose. Hence, this information, in combination with the discoveries and data presented herein, provides evidence that [$^{18}$F]-FDA can be used to probe specific aspects of gluconeogenesis and/or pathological conditions associated with aberrant gluconeogenesis.

Figure 4:
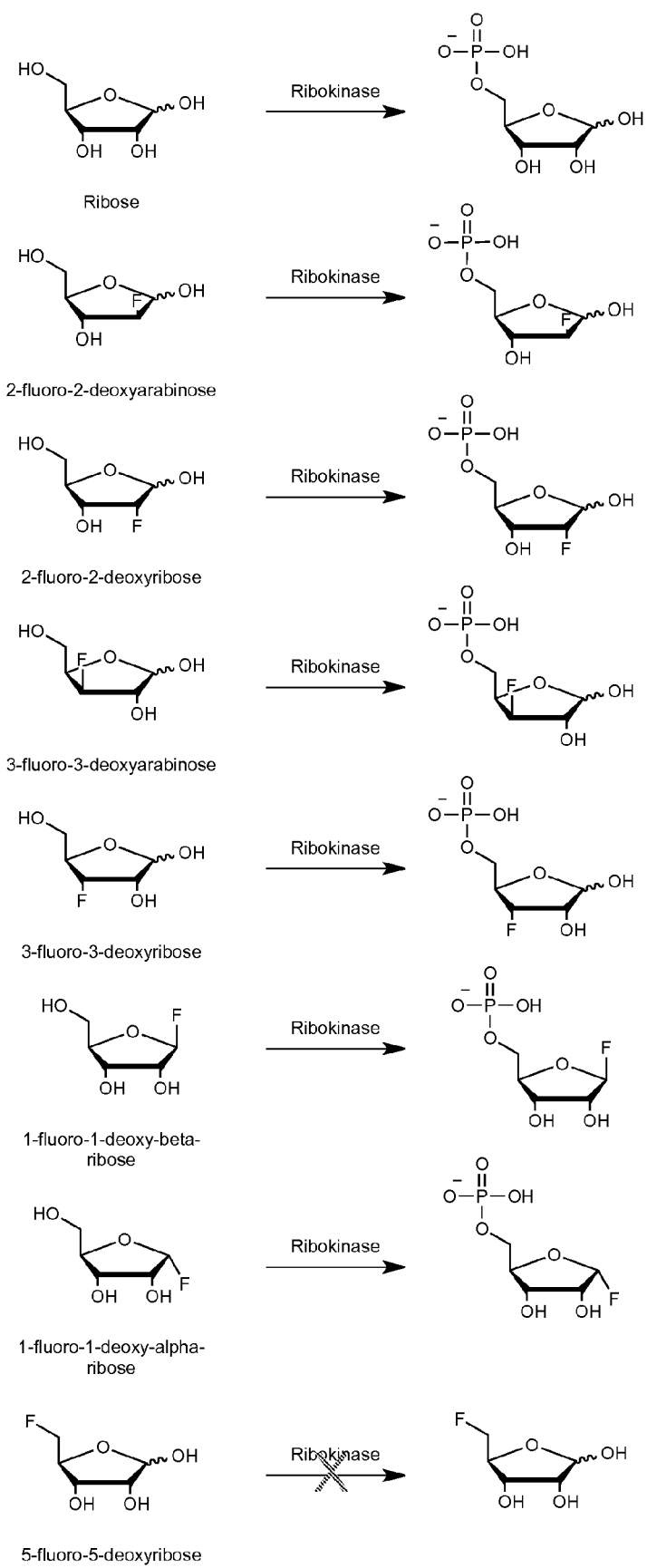
FIG. 4 provides information on cellular mechanisms associated with the accumulation of the disclosed PET probes in cells, a phenomena that, without being bound by a specific scientific theory or mechanism of action, appears to require the protein ribokinase. This figure illustrates chemical structures of various ribose compounds and the phosphorylated products that they form in the presence of ribokinase (high levels of which are found in the liver, kidney, and intestines).
Figure 5:
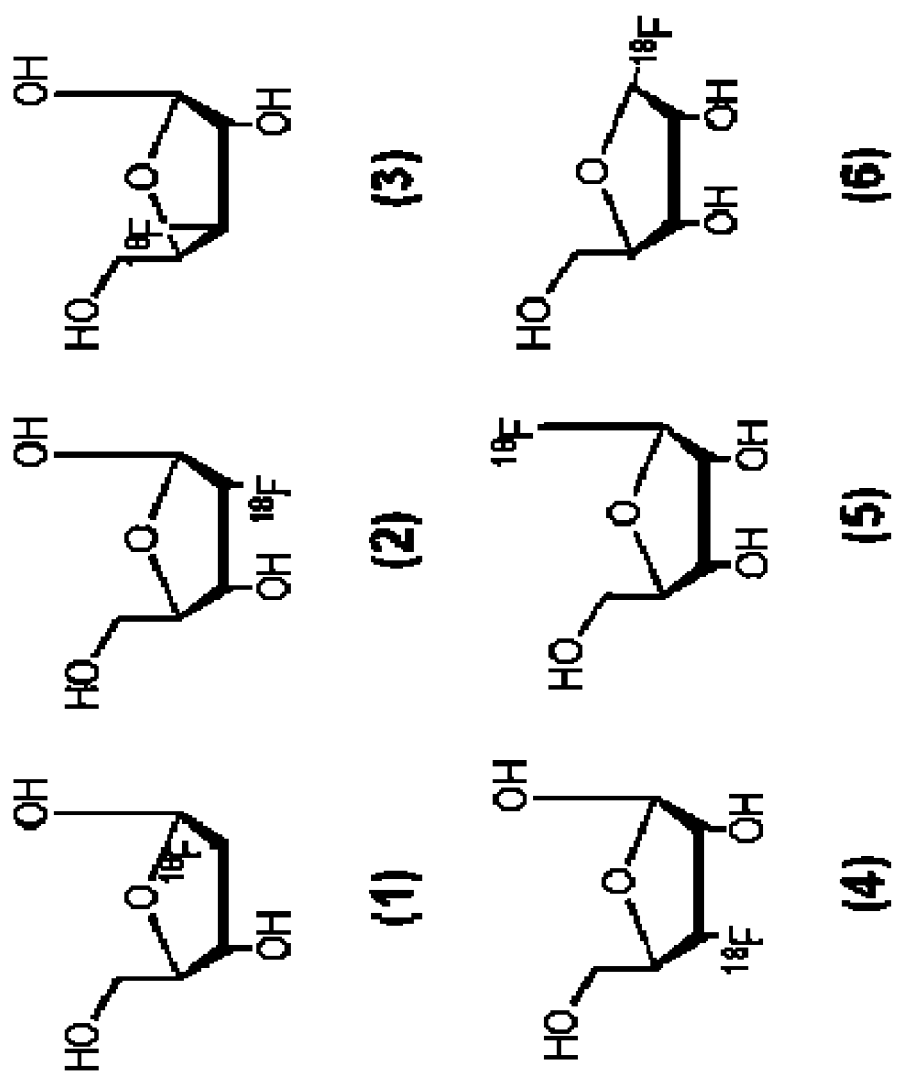
FIG. 5 illustrates chemical structures of [$^{18}F$]-labelled FDA compounds including (1) [$^{18}F$]-FDA; (2) [$^{18}F$]-2-fluoro-2-deoxyribose; (3) [$^{18}F$]-3-fluoro-3-deoxyarabinose; (4) [$^{18}F$]-3-fluoro-3-deoxyribose; (5) [$^{18}F$]-1-fluoro-1-deoxy-β-ribose; and (6) [$^{18}F$]-1-fluoro-1-deoxy-α-ribose.

Embodiments of the invention include compositions of matter comprising a positron emission tomography probe selected from the group of isomers consisting of: $^{18}$F labelled 2-fluoro-2-deoxyarabinose; 3-fluoro-3-deoxyarabinose; 2-fluoro-2-deoxyribose; 3-fluoro-3-deoxyribose; 1-fluoro-1-deoxy-alpha-ribose; and 1-fluoro-1-deoxy-beta-ribose (see, e.g. FIGS. 4 and 5). As shown in FIGS. 4 and 5, the ribose molecules of the invention are discrete compounds and not covalently coupled to other atom(s). The compositions of the invention can include a pharmaceutically acceptable carrier such as a diluent, a binding agent, or an agent selected for its ability to inhibit microbial growth. As discussed in detail below, it has been discovered that when these PET probes are administered to a subject, they selectively accumulate in certain tissues, a phenomena that can be observed via processes such as positron emission tomography. In working embodiments of the invention that are disclosed herein, positron emission tomography is used to show the selective accumulation of $^{18}$F labelled 2-fluoro-2-deoxyarabinose in murine liver, kidney and intestinal tissues.

Other embodiments of the invention include using the PET probes in methods of observing physiological characteristics in vivo, for example one or more physiological phenomena associated with cellular metabolism. Such methods comprise the steps of administering a composition to the mammal comprising a positron emission tomography probe selected from the group consisting of $^{18}$F labelled 2-fluoro-2-deoxyarabinose, 3-fluoro-3-deoxyarabinose, 2-fluoro-2-deoxyribose, 3-fluoro-3-deoxyribose, 1-fluoro-1-deoxy-alpha-ribose or 1-fluoro-1-deoxy-beta-ribose and then allowing the probe to accumulate in cells/tissues of the mammal The cells/tissues having this accumulated probe can then be observed using a positron emission tomography and/or computed tomography process (see. e.g. FIG. 2).

Figure 10:
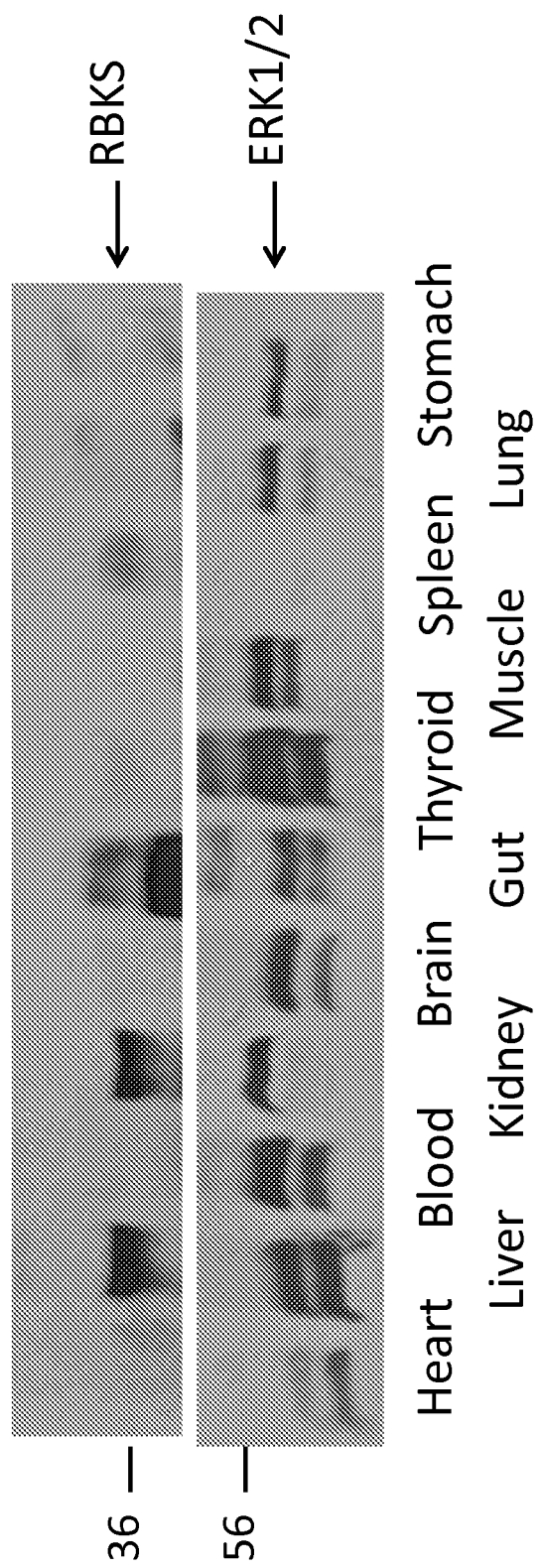
FIG. 10 provides data showing that Ribokinase is predominantly expressed in the liver, kidneys, and intestines, and that 2-fluoro-2-deoxyarabinose accumulates in organs with high levels of ribokinase. To obtain this data, organs from mice were lysed, resolved by SDS-PAGE, and immunoblotted with an anti-ribokinase and an anti-ERK1/2 antibody.

The PET probes disclosed herein have a number of desirable characteristics including an ability to specifically accumulate in distinct cell types, tissues or organs. Without being bound by a specific scientific theory or mechanism of action, it is believed that a cellular mechanism that leads to the observed accumulation of $^{18}$F in tissues such as the liver is the phosphorylation of the ribose probes by the protein ribokinase (see Park et al., FEBS Letters 581 (2007) 3211-3216 for a description of this ribokinase enzyme). This phosphorylation of the PET probes (at the 5'-position) by ribokinase is believed to alter the mobility of these molecules so that they accumulate in cells. FIG. 4 provides information on cellular mechanisms associated with the accumulation of the disclosed PET probes in cells and the phosphorylation of the hydroxyl group at the 5-position of these ribose molecules. FIG. 4 further illustrates chemical structures of various ribose compounds and the phosphorylated products that they form in the presence of ribokinase (high levels of which are found in the liver, kidney, and intestines). Because the hydroxyl group at the 5-position of the disclosed PET probes appears to require phosphorylation for $^{18}$F (the radionuclide of fluorine imaged in processes such as positron emission tomography) accumulation to occur in cells, the disclosed compounds will exhibit different in vivo accumulation profile as compared to compounds that are not amenable to phosphorylation by ribokinase (see, e.g. the compound disclosed in Onega et al., Chem. Commun., 2010, 46, 139-141). In this context, FIG. 10 provides data showing that Ribokinase is predominantly expressed in the liver, kidneys, and intestines, and that 2-fluoro-2-deoxyarabinose accumulates in these organs having high levels of ribokinase.

Embodiments of the invention use the disclosed PET probes to observe metabolic phenomena that are characteristic of certain biological processes. For example, in some embodiments of the invention a PET probe is used to examine cells for metabolic phenomena that are observed in disease syndromes such as cancer or diabetes. In other embodiments of the invention a PET probe is used to examine cells for metabolic phenomena that are observed in cells responding to a therapeutic agent such an anti-cancer agent or anti-diabetic agent administered to the mammal In illustrative embodiments of the invention a PET probe is used to examine cells for metabolic phenomena that are observed in cells responding to a therapeutic agent such as an oxythiamine, an insulin, an metformin, a leflunomide or a methotrexate composition. In a specific illustrative embodiment of the invention, the mammal is a human the PET probe consists of:

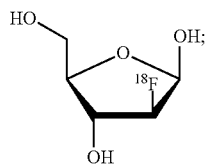

and cellular metabolism in liver, kidney, and/or intestinal tissues is selectively observed using a positron emission tomography process.

Embodiments of the invention can be adapted to monitor a number of physiological conditions including pathological syndromes. For example, embodiments of the invention can be used to monitor diseases in which the pentose phosphate or the de novo nucleotide synthesis pathways are dysregulated. Such diseases include, for example, neurodegenerative syndromes, syndromes characterized by ischemia, syndromes characterized by chronic inflammation, congestive heart failure, stroke and the like. In addition, embodiments of the invention can be used to monitor physiological responses to therapies that alter the activity of the pentose phosphate and de novo nucleotide synthesis pathways, including, for example, treatment with oxythiamine, insulin, metformin, leflunomide, and methotrexate. Embodiments of the invention can also be used to monitor a physiological activity of organs or tissues having ribose metabolism in vivo including the spleen, muscle, heart, thyroid, intestines, blood, kidney and liver.

Figure 6:
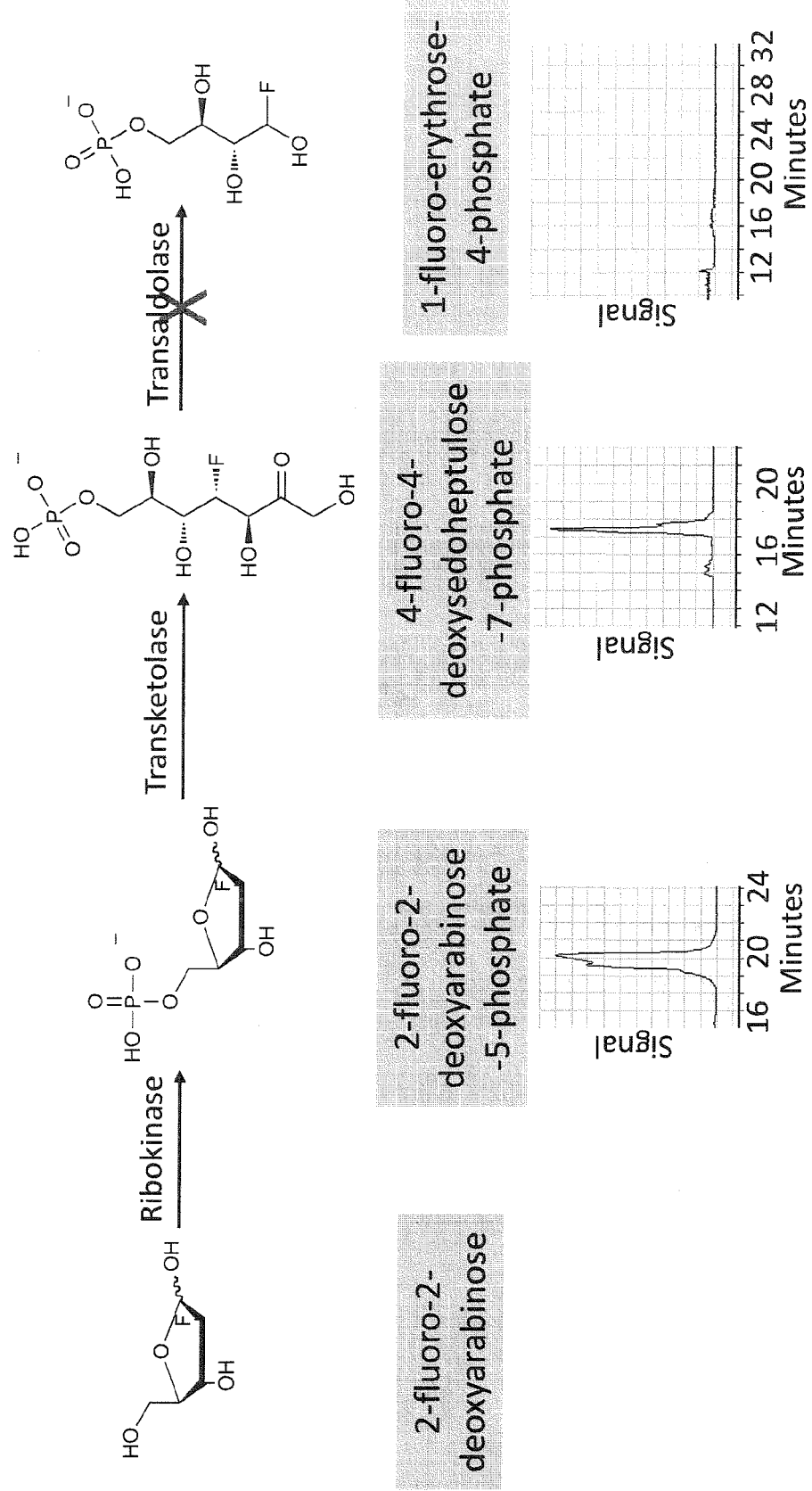
FIG. 6 provides data on which enzymes metabolize 2-fluoro-2-deoxyarabinose in vitro. This data shows that enzymes in the pentose phosphate pathway metabolize 2-fluoro-2-deoxyarabinose in vitro.
Figure 7:
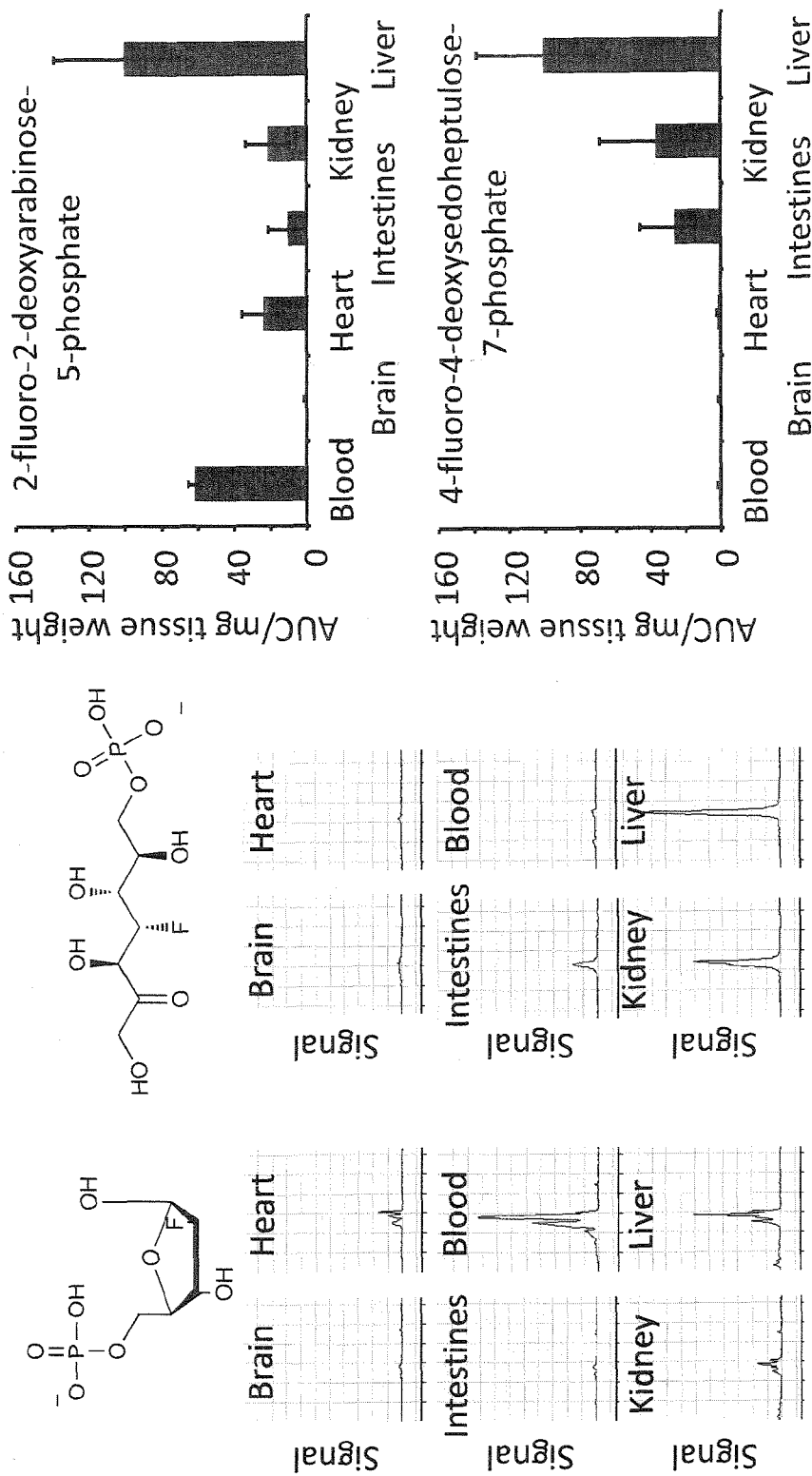
FIG. 7 provides data on which enzymes metabolize 2-fluoro-2-deoxyarabinose in vivo. This data shows that 2-fluoro-2-deoxyarabinose is metabolized in vivo by the non-oxidative pentose phosphate pathway to 4-fluoro-4-deoxysedoheptulose-7-phosphate.
Figure 8:
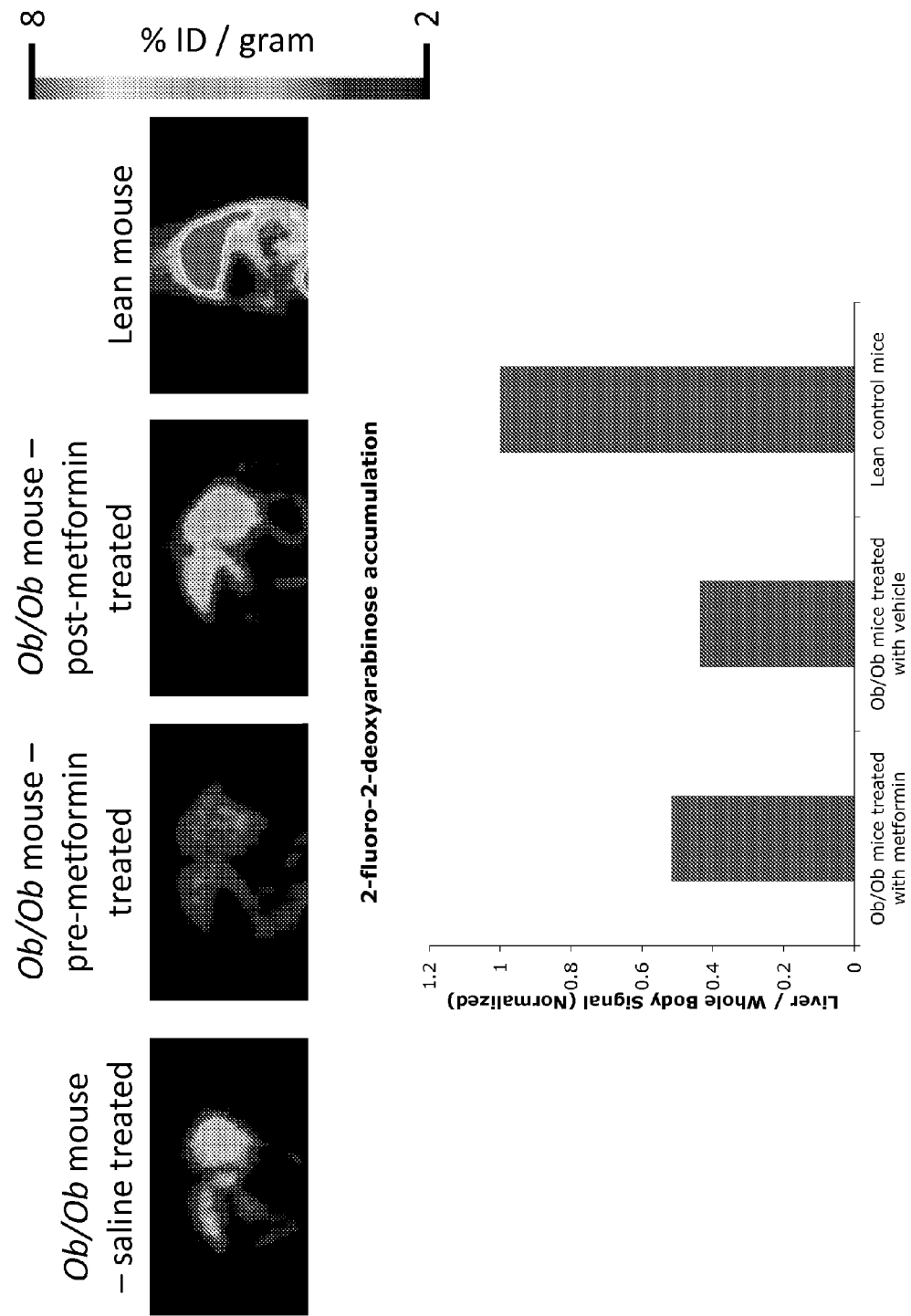
FIG. 8 provides data showing how 2-fluoro-2-deoxyarabinose can be used to image physiological conditions and/or responses to therapies (e.g. treatment with the therapeutic agent metformin) To obtain this data, Ob/Ob mice were imaged with [18F]-2-fluoro-2-deoxyarabinose. These mice were subsequently treated with saline or metformin (50 mg/kg) once a day for four days. On the fourth day, the mice were imaged with [18F]-2-fluoro-2-deoxyarabinose. The PET signal profile shows enhanced accumulation of this compound following treatment with metformin.
Figure 9:
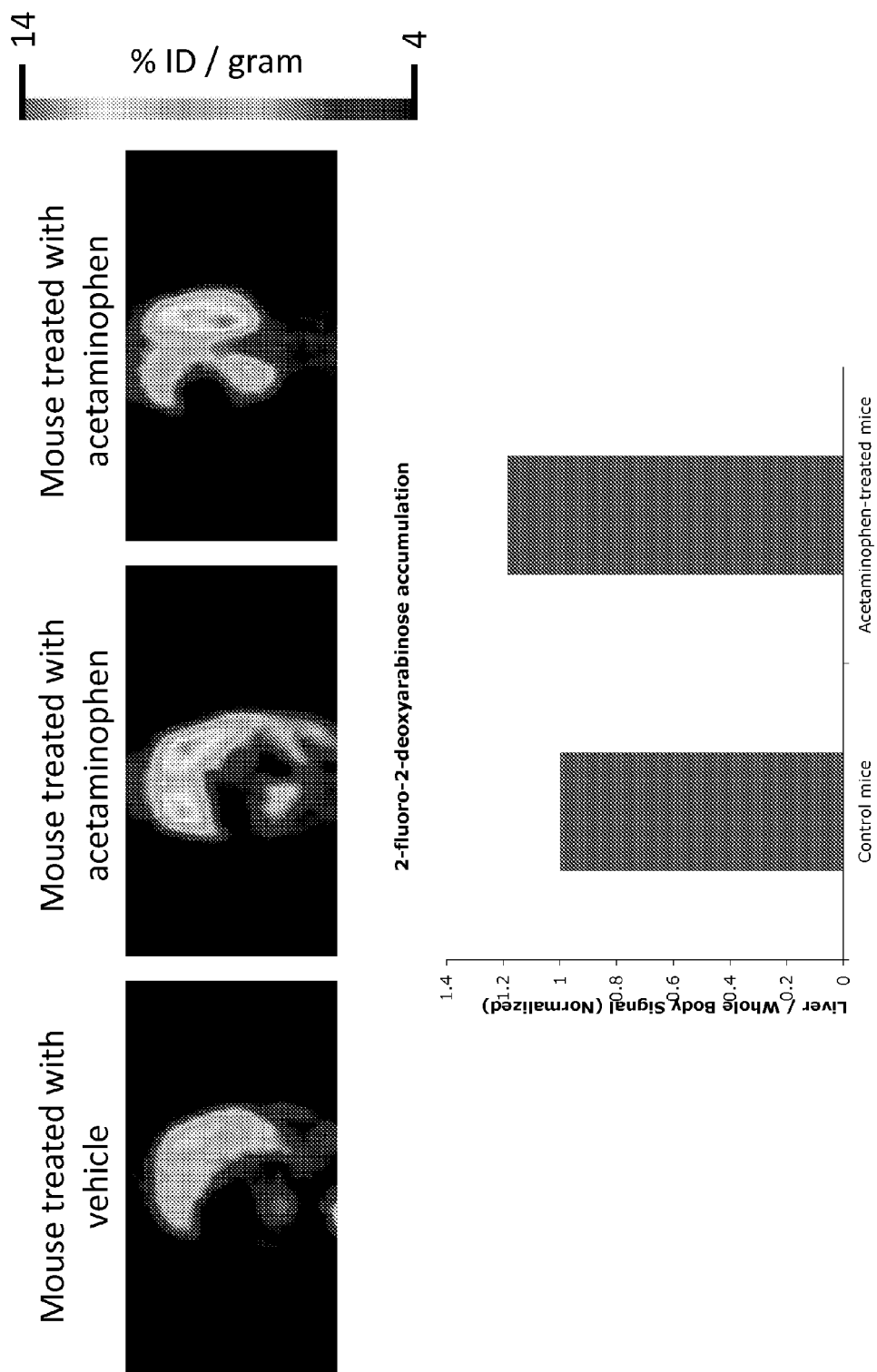
FIG. 9 provides data showing how 2-fluoro-2-deoxyarabinose can be used to image liver dysfunction. To obtain this data, mice were treated with acetaminophen (300 mg/kg) or vehicle. Four hours later, the mice were imaged using a [18F]-2-fluoro-2-deoxyarabinose PET probe.

The data shown, for example, in FIGS. 6 and 7 includes metabolite studies that show that enzymes in the pentose phosphate pathway metabolize $^{18}$F labelled 2-fluoro-2-deoxyarabinose so of a probe in vitro and in vivo (FIGS. 6 and 7). This provides evidence that such working embodiments can be used to monitor changes in the pentose phosphate pathway, caused either by disease or therapeutic agents. Other derivatives of this working embodiment may be metabolized by the de novo nucleotide synthesis pathway and used in the same way. The data shown, for example, in FIGS. 6 and 7 includes metabolite studies that show that $^{18}$F labelled 2-fluoro-2-deoxyarabinose is metabolized by tissues in addition to the liver, including the spleen, muscles, heart, blood, thyroid, and kidneys (FIG. 7). This was unexpected, and although this probe predominantly accumulates in the liver during physiological conditions, the fact that other tissues metabolize the probe provides evidence that under pathological conditions, these tissues accumulate significant levels of the probe as well. This data provides evidence that the probe may access a variety of tissues in addition to the liver, including the spleen, muscles, heart, blood, thyroid, and kidneys.

Embodiments of the invention include methods of selectively observing an in vivo tissue or organ in a mammal such as liver, kidney, and/or intestinal tissues using a PET probe ribose isomer in a positron emission tomography and computed tomography process. In illustrative embodiments of the invention, liver, kidney, salivary gland and/or intestinal tissue is imaged. Moreover, mass spectrometry data provides evidence that the heart, blood, and spleen tissues accumulate the PET probes disclosed herein. In addition, in certain diseases and/or dysfunction, tissues may become more visible when exposed to a PET probe. For example, the literature teaches that, following ischemic insult, heart tissues accumulate high levels of ribose, a phenomenon that can be imaged using embodiments of the invention.

Methods of selectively observing an in vivo tissue or organ in a mammal typically comprise the steps of administering a composition to the mammal that includes a positron emission tomography probe selected from the group consisting of 2-fluoro-2-deoxyarabinose, 3-fluoro-3-deoxyarabinose, 2-fluoro-2-deoxyribose, 3-fluoro-3-deoxyribose, 1-fluoro-1-deoxy-alpha-ribose, and 1-fluoro-1-deoxy-beta-ribose. Typically in these methods, the positron emission tomography probe is administered to the mammal in combination with a pharmaceutically acceptable compound comprising a diluent, a carrier, or a binding agent. Following this administration, the probe then selectively accumulates in tissues or organs having cells that express ribokinase such as liver, kidney, and/or intestinal tissues. The probe can be used to observe an in vivo tissue or organ where it has accumulated, typically by using a positron emission tomography and/or a computed tomography process. In this way, a mammalian tissue or organ such as liver, kidney, and/or intestinal tissues can be selectively observed in vivo.

Embodiments of the invention can use the disclosed PET probes to observe metabolic phenomena that are characteristic of certain biological processes such as the cellular metabolism in liver, kidney, and/or intestinal tissues. For example, some embodiments of observed cellular metabolism in such a tissue to detect the presence or absence of metabolic phenomena that are characteristic of a metabolic disorder, tumor growth, gluconeogenesis, a neurodegenerative syndrome, a syndrome characterized by ischemia, a syndrome characterized by chronic inflammation, congestive heart failure, stroke or the like. Similar embodiments of the invention include methods for observing a physiological activity in the liver that is observed in liver dysfunction, liver cancer or liver regeneration.

Embodiments of the invention include methods to synthesize the compounds disclosed herein (see Example 1 below and FIG. 11). Briefly, in one exemplary implementation, the synthesis of the [$^{18}$F]-FDA and its purification is carried out as follows: Using a RDS-111 cyclotron, non-carrier-added [$^{18}$F]-fluoride ion is produced by 11 MeV proton bombardment of 98% enriched [$^{18}$O] water in a silver target. 100 microL of aqueous [$^{18}$F]-fluoride ion is treated with a solution of $K_2CO_3$ (1.5 mg) dissolved in 14 microL water and Kryptofix K222 (10 mg) dissolved in 950 microL of anhydrous acetonitrile and then mixed. The mixture is heated at 105 degrees Celsius and evaporated under nitrogen flow and vacuum for 7 min with two 1 mL anhydrous acetonitrile additions to complete the azeotropic distillation. 2-O-(Trifluoromethylsulfonyl)-1,3,5-tri-O-benzoyl-alpha-D-ribofuranose is added to the dry complex and the reaction mixture is heated at 155 degrees Celsius for 15 min under sealing conditions. After the fluorination, the solution is cooled to 40 degrees Celsius and loaded into a silica cartridge. [$^{18}$F]-2-fluoro-2-deoxy-1,3,5-tri-O-benzoyl-alpha-ribofuranose is eluted from the cartridge with 2 mL of anhydrous ethyl acetate into a second vessel. The anhydrous ethyl acetate is evaporated at 60 degrees Celsius under nitrogen flow and vacuum for 3 min. To the dry product, 500 microL of sodium methoxide (0.5 M in methanol) is added and the mixture is heated at 100 degrees Celsius for 5 min under sealed conditions. The mixture is purified on a SPK column system consisting of a SCX maxi clean cartridge (preconditioned with 10 mL water) followed by an alumina cartridge (preconditioned with 10 mL water) and a C18 cartridge (preconditioned with 6 mL anhydrous ethanol followed by 10 mL water). The [$^{18}$F]-fluororibose is finally eluted from the column system with sterile water and sterilized by passing it through a 0.22 micrometer filter. The radiochemical purity is determined by radio TLC and is ~99% pure. Overall purity is determined using a radio analytical HPLC consisting of a Phenomenex luna column (25 cm×0.46 cm, 5 u particle size) eluted with mobil phase (1-9% Ethanol-water v/v) and monitored with a gamma radio detector (Bioscan), and UV detector (200 nm).

Another embodiment of the invention is a method of forming [$^{18}$F]-2-fluoro-2-deoxyribose. As discussed in Example 1 below, this method combines isopropyl 2-O-(trifluoromethylsulfonyl)-3,5-di-O-(4-nitrobenzyl)-beta-D-arabinofuranoside with [$^{18}$F]-fluoride ion and CH3CN so as to form a first mixture. In this embodiment, this mixture is then loaded on to and then eluted from silica matrix. Isopropyl 2-O-(trifluoromethyl-sulfonyl)-3,5-di-O-(4-nitrobenzyl)-β-D-arabinofuranoside is then eluted from the silica matrix. Raney Nickel is then added to the Isopropyl 2-O-(trifluoromethyl-sulfonyl)-3,5-di-O-(4-nitrobenzyl)-β-D-arabinofuranoside to form a second mixture comprising [$^{18}$F]-2-fluoro-2-deoxyribose. Detailed methods and materials associated with such methods are discussed in Example 1 below and shown in FIG. 11 (e.g. purification steps using a cartridge comprising alumina and the like).

Another embodiment of the invention is a method of forming [$^{18}$F]-3-fluoro-3-deoxyarabinose. As discussed in Example 1 below, this method comprises the steps of combining 1,2-O-isopropilydene-3-O-(trifluoromethylsulfonyl)-5-O-triphenylmethyl-lyxofuranoside with [$^{18}$F]-fluoride ion and CH3CN so as to form a first mixture comprising 3a as shown in FIG. 11. 3a is then combined with trifluoroacetic acid and water to form a second mixture, wherein the second mixture forms [$^{18}$F]-3-fluoro-3-deoxyarabinose. Another embodiment of the invention is a method of forming 3-fluoro-3-deoxyribose. As discussed in Example 1 below, this method comprises the steps of combining 1,2-O-benzylidene-3-O-(trifluoromethylsulfonyl)-5-O-triphenylmethyl-xylofuranoside with [$^{18}$F]-fluoride ion and CH3CN so as to form a first mixture comprising 4a as shown in FIG. 11. 4a is then combined with trifluoroacetic acid and water to form a second mixture, wherein the second mixture forms [$^{18}$F]-3-fluoro-3-deoxyribose. Detailed methods and materials associated with such methods are discussed in Example 1 below and shown in FIG. 11 (e.g. purification steps using a cartridge comprising alumina and the like).

In typical embodiments of the present invention, a PET probe compound(s) such as one or more of those described above is synthesized and purified and then injected into a mouse. After approximately 1 hour, the mouse can be imaged by a process such as PET/CT. In an exemplary implementation, 40-200 microCi of probe is injected intravenous into a mouse. Following one hour of uptake, the mouse is imaged on a microPET imaging system. In this way, the PET probes disclosed herein can be used as diagnostic tools, radio tracers, monitoring agents and the like in various diagnostic methods, for example in in vivo imaging (e.g. selective imaging of the liver). In this context, artisans can utilize and/or adapt existing PET methods and materials to practice embodiments of the invention disclosed herein. See, for example, Radu, C. G. et al., *Nat Med.* 2008 July; 14(7):783-8 (2012), Positron emission tomography probes for imaging immune activation and selected cancers; U.S. Pat. No. 8,101,740; as well as *Positron Emission Tomography* by Anatoliy Granov, Leonid Tiutin and Thomas Schwarz (2013); *Basics of PET Imaging: Physics, Chemistry, and Regulations* by Gopal B. Saha (2010); and *Positron Emission Tomography* (*Methods in Molecular Biology*) by Malik E. Juweid and Otto S. Hoekstra (2011), the contents of which are incorporated by reference). See also Haradahira et al., Nucl. Med. Biol. Vol. 22. No. 6. 719-725 (1995) and U.S. Pat. No. 8,241,607, the contents of which are incorporated by reference. In embodiments of the invention, methods for detecting the labelled isomer of the present invention may include Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

In typical embodiments of the invention, the PET probes are used imaging tracers that detect and quantify cancer/tumor cell densities within live tissues. For live tissue imaging, preferably the radiotracers of the invention can be administered to subjects in an amount suitable for in vivo imaging thereof, and to locate, diagnose, identify, evaluate, detect and/or quantify cancer cells. Generally, a unit dosage comprising a PET probe radiotracer of the invention may vary depending on subject or patient considerations. Such considerations include for example, age, condition, sex, extent of disease, contraindications, or concomitant therapies.

The PET probe imaging compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes. Thus, the present compounds may be systemically administered, e.g., orally, in combination with a pharmaceutically acceptable vehicle such as an inert diluent or an edible carrier. They may be enclosed in hard or soft shell gelatin capsules, may be compressed into tablets, or may be incorporated directly with the food of the patient's diet. For oral administration, the PET probes disclosed herein may be combined with one or more excipients and used in the form of ingestible tablets, buccal tablets, troches, capsules, elixirs, suspensions, syrups, wafers, and the like.

Tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the probe, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the probe may be incorporated into sustained-release preparations and devices.

The probe may also be administered, for example, intravenously or intraperitoneally by infusion or injection. Solutions of the probe or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the probe in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Agents such as flavorings and additional antimicrobial agents can be added to optimize the properties for a given use.

As noted above, the PET probe compounds of the invention can be administered to a subject or patient with other therapeutic agents that may be useful in the treatment of a pathological condition such as diabetes or cancer. One such embodiment of the invention is a method for administering an effective amount of one or more compounds of the invention to a subject suffering from or believed to be at risk of suffering from a pathological condition such as diabetes or cancer. The method also comprises administering either sequentially or in combination with one or more compounds of the invention, a conventional therapeutic measure protocol, or agent that can potentially be effective for the treatment or prophylaxis of a pathological condition such as diabetes or cancer.

Administration of a PET probe compositions of the invention to a subject may be local or systemic and accomplished orally, intradermally, intramuscularly, subcutaneously, intravenously, intra-aterially or intrathecally (by spinal fluid); or via powders, ointments, drops or as a buccal or nasal spray. A typical composition for administration can comprise a pharmaceutically acceptable carrier for the compound or radiotracer of the invention. Pharmaceutically acceptable carrier include, without limitation, aqueous solutions, non-toxic excipients comprising salts, preservative or buffers, amongst others known within the art.

The following examples provide illustrative methods and materials that can be used with embodiments of the invention.

EXAMPLES

Example 1

Illustrative Methods for Making Embodiments of the Invention

Materials and Methods

[$^{18}$F]-FDA Synthesis (1). The synthesis of the [$^{18}$F]-FDA and its purification was carried out as follows: Using a RDS-111 cyclotron, non-carrier-added [$^{18}$F]-fluoride ion was produced by 11 MeV proton bombardment of 98% enriched [$^{18}$O] water in a silver target. 100 μL of aqueous [$^{18}$F]-fluoride ion was treated with a solution of $K_2CO_3$ (1.5 mg) dissolved in 14 μL water and Kryptofix K222 (10 mg) dissolved in 950 μL of anhydrous acetonitrile and then mixed. The mixture was heated at 105° C. and evaporated under nitrogen flow and vacuum for 7 min with two 1 mL anhydrous acetonitrile additions to complete the azeotropic distillation. 2-O-(Trifluoromethylsulfonyl)-1,3,5-tri-O-benzoyl-alpha-D-ribofuranose (Advanced Biochemical Compounds) was added to the dry complex and the reaction mixture was heated at 155° C. for 15 min under sealing conditions. After the fluorination, the solution was cooled to 40° C. and loaded into a silica cartridge. [$^{18}$F]-2-Fluoro-2-deoxy-1,3,5-tri-O-benzoyl-alpha-ribofuranose was eluted from the cartridge with 2 mL of anhydrous ethyl acetate into a second vessel. The anhydrous ethyl acetate was evaporated at 60° C. under nitrogen flow and vacuum for 3 min. To the dry product, 500 μL of sodium methoxide (0.5 M in methanol) was added and the mixture was heated at 100° C. for 5 min under sealed conditions. The mixture was purified on a SPK column system consisting of a SCX maxi clean cartridge (preconditioned with 10 mL water) followed by an alumina cartridge (preconditioned with 10 mL water) and a C18 cartridge (preconditioned with 6 mL anhydrous ethanol followed by 10 mL water). The [$^{18}$F]-fluororibose was finally eluted from the column system with sterile water and sterilized by passing it through a 0.22 micrometer filter. The radiochemical purity was determined by radio TLC and was ~99% pure. Overall purity was determined using a radio analytical HPLC consisting of a Phenomenex luna column (25 cm×0.46 cm, 5 u particle size) eluted with mobil phase (1-9% Ethanol-$H_2O$ v/v) and monitored with a gamma radio detector (Bioscan), and UV detector (200 nm).

Figure 11A:
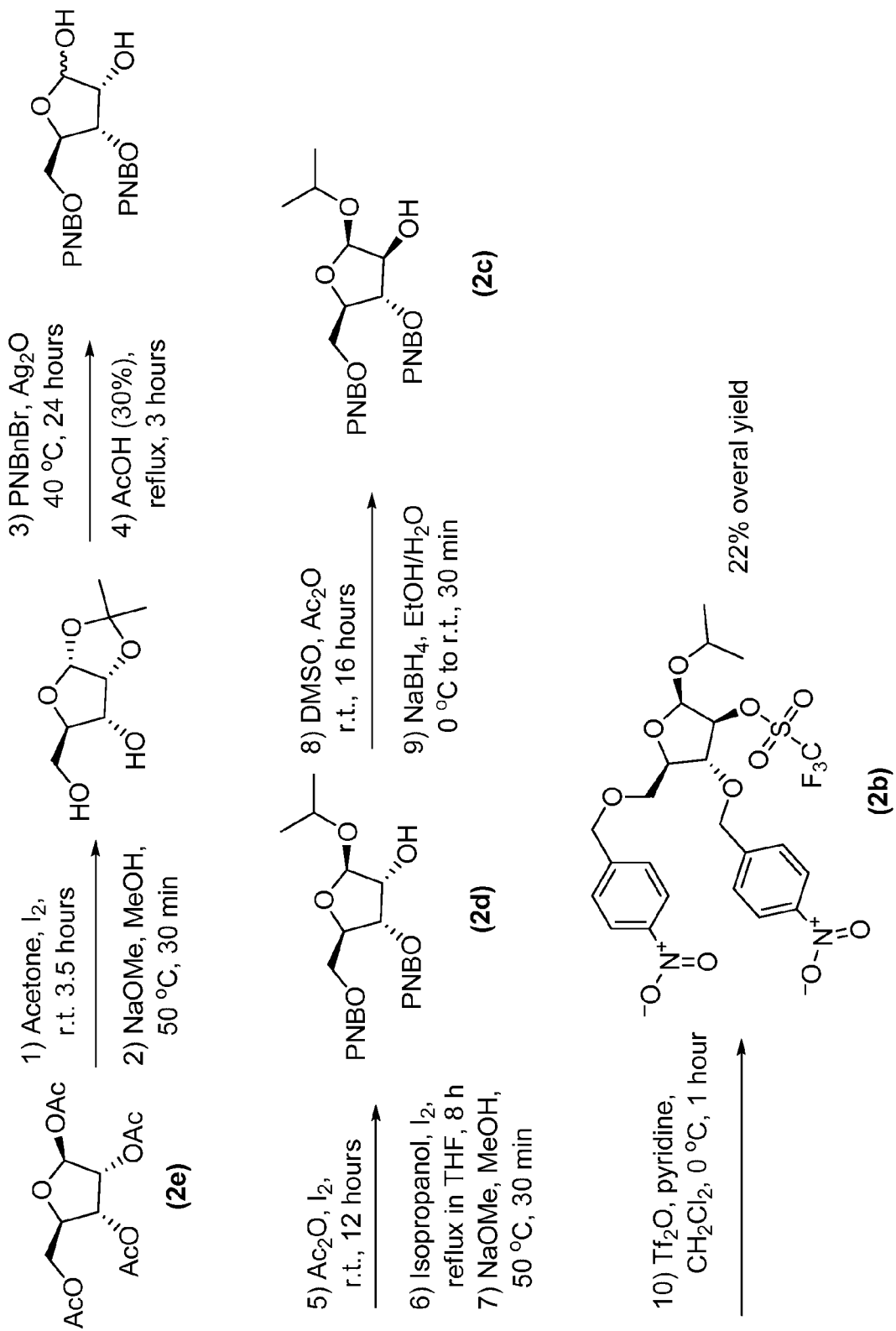
FIG. 11A shows scheme 1, the synthesis of Isopropyl 2-O-(trifluoromethylsulfonyl)-3,5-di-O-(4-nitrobenzyl)-beta-D-arabinofuranoside (2b).

[$^{18}$F]-2-Fluoro-2-deoxyribose Synthesis (2). Isopropyl 2-O-(trifluoromethyl-sulfonyl)-3,5-di-O-(4-nitrobenzyl)-β-D-arabinofuranoside (2a) was prepared in ten steps according to Scheme 1 as shown in FIG. 11A.

To a solution of 3.05 g (9.6 mmol) 1,2,3,5-tetra-O-acetyl-β-ribofuranose (2e) in 30 mL of dry (4 A molecular sieves for 4 hours) acetone was added 0.6 g (2.4 mmol) of elemental iodine and the reaction was stirred under argon at room temperature for 3.5 hours. Methylene chloride (100 mL) were added and the reaction was washed with $NaHCO_3$ (20 mL saturated aqueous solution) followed by $Na_2S_2O_3$ (20 mL of 10% aqueous solution). The aqueous fractions were extracted with 2×30 mL of $CH_2Cl_2$ and the combined organic fractions were washed with 50 mL of brine, dried with $Na_2SO_4$ and the solvent was removed via rotary evaporation. The crude material was dissolved in 30 mL of dry MeOH and 0.2 g of NaOMe was added to the solution. The reaction was stirred for 30 min at 50° C. Once TLC (4% MeOH in $CH_2Cl_2$) showed a single spot with Rf=0.34, Amberlyst-15 resin was added to neutralize the reaction. The resin beads were removed by filtration and mother liquor was removed via rotary evaporation. The crude material was co-evaporated with 10 mL of toluene and mixed with 10 g (43 mmol) of $Ag_2O$ and 10 g of activated (150° C. for 3 days) 4Å molecular sieves. The solids were suspended in 80 mL of dry $CH_2Cl_2$ and stirred for 1 hour, then 6.5 g (28 mmol) of 4-nitrobenzyl bromide was introduced and the reaction was stirred at 40° C. under argon for 16 hours. The reaction was filtered through Celite washed with 3×15 mL of $CH_2Cl_2$ and dried under vacuum. The crude material was dissolved in AcOH (50 mL of 30% aqueous solution) and refluxed for 3 hours. The solvent was then removed under high vacuum and the crude material was sonicated with 50 ml of a 1/9 EtOAc/hexanes mixture, which was decanted upon cooling in an ice water bath. The remaining solid was dried under high vacuum and dissolved in 10 mL of acetic anhydride along with 0.015 g of $I_2$. The reaction was stirred overnight at 17° C. TLC (1/2 EtOAc/hexanes) indicated a single spot with Rf=0.3. The reaction mixture was dried under vacuum and the crude material was extracted from $NaHCO_3$ (10 ml of saturated solution) with 3×50 mL of $CH_2Cl_2$. The organic phases were combined and dried over $Na_2SO_4$ and the solvent was removed via rotary evaporation. The crude material was dissolved in 15 mL of dry THF. To that solution were added iodine (0.35 g, 1.39 mmol) and dry (4 A mol. sieves overnight) isopropanol (2 mL, 27 mmol) and the reaction was refluxed under argon for 8 hours. The solvent was rotary evaporated and dissolved in 100 mL of $CH_2Cl_2$. The solution was washed with $NaHCO_3$ (20 mL saturated aqueous solution) followed by $Na_2S_2O_3$ (20 mL of 10% aqueous solution), dried over $Na_2SO_4$ and evaporated under vacuum. The crude material was dissolved in 30 mL of dry MeOH and 0.2 g of NaOMe was added to the solution. The reaction was stirred for 30 min at 50° C. TLC (EtOAc/hexanes=1/2) showed one major spot with Rf=0.18. Amberlyst-15 resin was added to neutralize the reaction. The resin beads were removed by filtration and the solvent was completely removed using rotary evaporation. The crude material was chromatographed on silica gel eluting with a gradient of 20% to 40% of EtOAc in hexanes to afford 1.98 g of 2d: $^1$H NMR (300 MHz, $CDCl_3$) δ 8.18 (dd, J=8.9, 2.0 Hz, 2H), 8.14 (dd, J=8.9, 2.0 Hz, 2H), 7.48 (dd, J=8.8, 2.2 Hz, 2H), 7.46 (dd, J=8.9, 2.0 Hz, 2H), 5.09 (s, 1H), 4.72 (d, J=12.9 Hz, 1H), 4.69 (d, J=12.9 Hz, 1H), 4.67 (s, 2H), 4.27 (ddd, J=5.7, 5.7, 5.0 Hz, 1H), 4.13 (dd, J=4.8, 4.8 Hz, 1H), 4.12 (m, 1H), 3.89 (septet, J=6.1 Hz, 1H), 3.67 (dd, J=10.2, 5.0 Hz, 1H), 3.65 (dd, J=10.2, 5.7 Hz, 1H), 2.54 (d, J=3.4 Hz, 1H), 1.13 (d, J=6.3 Hz, 3H), 1.09 (d, J=6.3 Hz, 3H).

The ribofuranoside (2d) was dissolved in 16 mL of a mixture of 4/1 DMSO/$Ac_2O$ and stirred at room temperature for 18 hours. TLC (50% EtOAc in hexanes) indicated a single, slightly higher spot. The reaction was dissolved in $CH_2Cl_2$ (100 mL) and washed with water 2×100 mL and the organic layer was dried with $Na_2SO_4$ and the solvent was removed via rotary evaporation. The crude material was dissolved in 10 mL of a 7:1:2 $EtOH:H_2O:CH_2Cl_2$ mixture and $NaBH_4$ (0.8 g) was added with stirring at 0° C. for 30 min. The reaction was then warmed to ambient temperature and quenched with 10% AcOH (30 mL). The mixture was extracted from $NaHCO_3$ (sat. 100 mL) with 2×100 mL of EtOAc, the combined organic layer was washed with 2×100 mL of water and then dried over $Na_2SO_4$. The solvent was removed under vacuum. Column chromatography of the residue on silica gel (30% to 50% of EtOAc in hexanes) afforded 2c: $^1$H NMR (300 MHz, $CDCl_3$) δ 8.20 (dd, J=8.9, 2.0 Hz, 2H), 8.16 (dd, J=8.9, 2.0 Hz, 2H), 7.50 (dd, J=8.9 Hz, 2H), 7.47 (d, J=8.9 Hz, 2H), 5.11 (d, J=4.5 Hz, 1H), 4.92 (d, J=13.3 Hz, 1H), 4.76 (d, J=13.3 Hz, 1H), 4.67 (s, 2H), 4.27 (ddd, J=9.4, 6.1, 4.9 Hz, 1H), 4.13 (ddd, J=5.8, 5.8, 5.7 Hz, 1H), 3.96 (septet, J=6.1 Hz, 1H), 3.85 (dd, J=5.9, 5.9 Hz, 1H), 3.65 (d, J=5.8 Hz, 2H), 2.64 (d, J=9.4 Hz, 1H), 1.19 (d, J=6.2 Hz, 3H), 1.15 (d, J=6.2 Hz, 3H).

To a solution of 0.025 g (0.054 mmol) of the ribofuranoside (2c) and 0.066 mL (0.81 mmol) of pyridine in 1 mL of dry $CH_2Cl_2$ was added $Tf_2O$ (0.11 mL of 1 M solution in $CH_2Cl_2$) at 0° C. The reaction was stirred under argon in an ice-bath for 30 min, then quenched with 5 mL of a 1:1 mixture of ice and saturated $NaHCO_3$ solution. The mixture was extracted with 2×10 mL of $CH_2Cl_2$, the combined organic layer was dried over $Na_2SO_4$, and dried under high vacuum at 17° C. To this was added 5 ml of n-heptane and the resulted suspension was dried under high vacuum at 17° C. The crude triflate obtained (31 mg, 97%) 2b was 99% pure. 2b: $^1$H NMR (300 MHz, $CDCl_3$) δ 8.22 (dd, J=8.9, 2.0 Hz, 2H), 8.16 (dd, J=8.9, 2.0 Hz, 2H), 7.50 (d, J=8.9 Hz, 2H), 7.42 (d, J=8.9 Hz, 2H), 5.25 (d, J=4.5 Hz, 1H), 5.09 (dd, J=6.3, 4.9 Hz, 1H), 4.73 (s, 2H), 4.67 (s, 2H), 4.34 (dd, J=6.6, 5.1 Hz, 1H), 4.17 (ddd, J=6.7, 5.8, 5.7 Hz, 1H), 3.92 (septet, J=6.1 Hz, 1H), 3.69 (dd, J=9.9, 5.7 Hz, 1H), 3.66 (dd, J=9.9, 6.4 Hz, 1H), 1.19 (d, J=6.2 Hz, 3H), 1.18 (d, J=6.2 Hz, 3H).

Figure 11B:
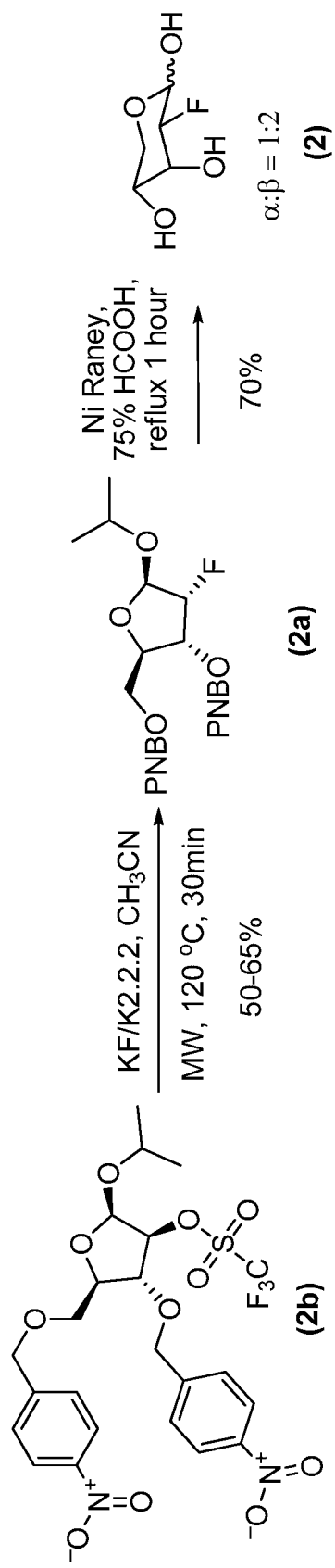
FIG. 11B shows Scheme 2, the synthesis of 2-fluoro-2-deoxyribose (2).

Scheme 2 as shown in FIG. 11B illustrates the synthesis of 2-fluoro-2-deoxyribose (2). 13 mg (34.58 μmol) of Kryptofix 222 ($K_{222}$), 18 μl of 1 M of aqueous $K_2CO_3$ solution, and 0.9 ml of anhydrous MeCN was placed into the reaction vessel inside the cavity of the microwave (MW). [$^{18}$F]fluoride solution in [$^{18}$O]$H_2O$ from the cyclotron was added and mixed with a magnetic stir bar. The vacuum was applied to the mixed solution under nitrogen flow (5 psi) and it was exposed 5 times to 20 W power for 2 min with two additions of acetonitrile, to complete the drying and remove the water by azeotropic evaporation and form the $K_{222}$/[$^{18}$F]F complex.

To the $K_{222}$/[$^{18}$F]F complex was added the 5 mg of the fully protected precursor dissolved in 500 µl of acetonitrile and heated in the microwave cavity at 115° C. at 40 watts potency for 20 min. The reaction mixture is then loaded in a silica Sep-pak cartridge preconditioned with hexane and eluted with 2 mL of ethyl acetate. The solvent is evaporated at 82° C. in oil bath and under nitrogen until dryness.

100 mg of Ni-Raney was added with 200 µl of formic acid and the reaction mixture was heated at 76° C. for 15 min, filtered with a polypropylene filter 0.45 nm. 10% EtOH/water was added to rinse the filter. The mixture was loaded onto an ion and anion exchange column followed by tC18 cartridge and alumina cartridge and passed through a millipore filter (0.22 um).

The eluted product is 2-fluoro-2-deoxy-ribose. The radiochemical purity was determined by radio TLC and is ~99% pure.

Figure 11C:
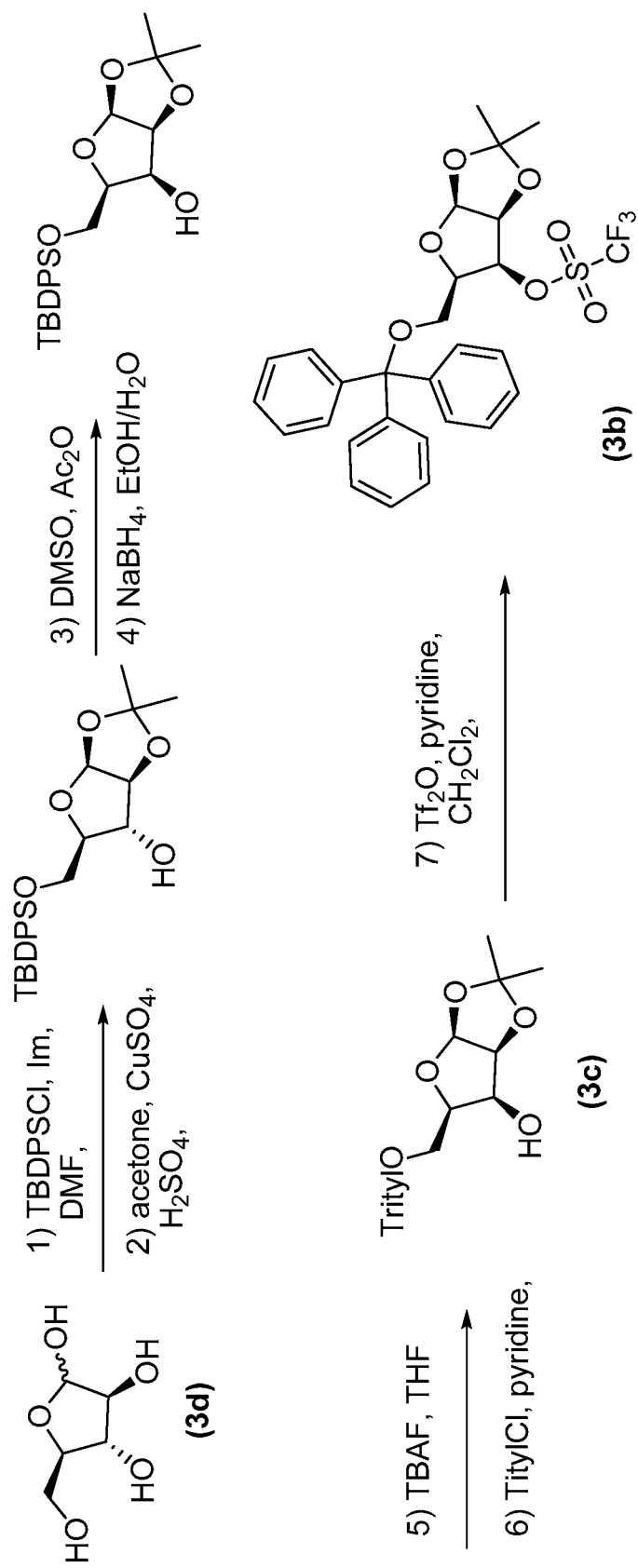
FIG. 11C shows Scheme 3, the synthesis of 1,2-O-isopropilydene-3-O-(trifluoromethylsulfonyl)-5-O-triphenylmethyl-lyxofuranoside (3b).

[$^{18}$F]-3-Fluoro-3-deoxyarabinose Synthesis (3). 1,2-O-Isopropylidene-3-O-(trifluoromethanesulfonyl)-5-O-triphenylmethyl-lyxofuranoside (3b) was prepared according to Scheme 3. Scheme 3 as shown in FIG. 11C illustrates the synthesis of 1,2-O-isopropylidene-3-O-(trifluoromethanesulfonyl)-5-O-(triphenylmethyl)lyxofuranoside (3b).

Figure 11D:
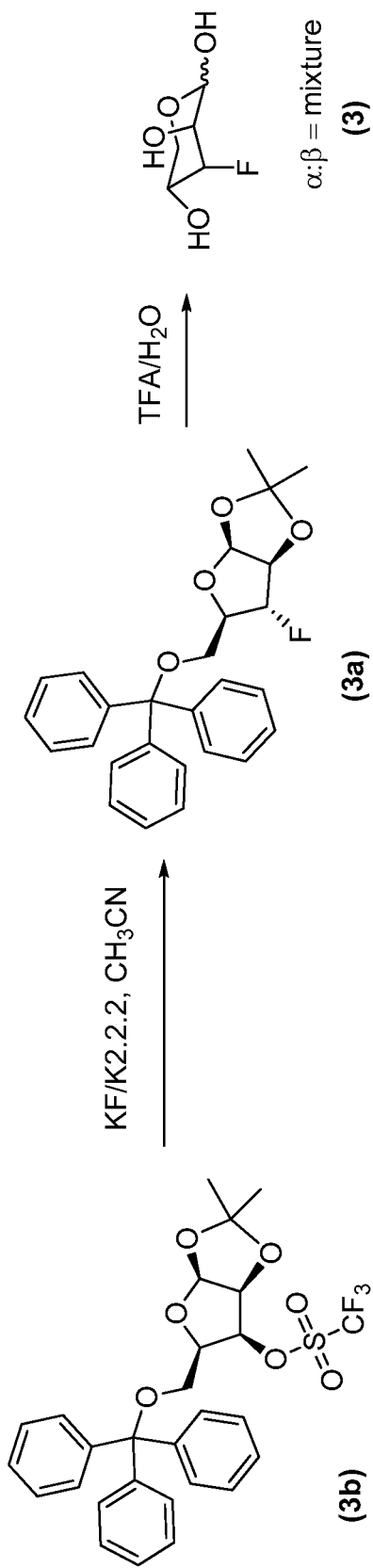
FIG. 11D shows Scheme 4, the synthesis of 3-fluoro-3-deoxyarabinose (3).

Fluorination, deprotection, and purification were performed as described above for [$^{18}$F]-FDA with modifications according to Scheme 4 as shown in FIG. 11D. Scheme 4 as shown in FIG. 11B illustrates the synthesis of 3-fluoro-3-deoxyarabinose Synthesis (3).

Figure 11E:
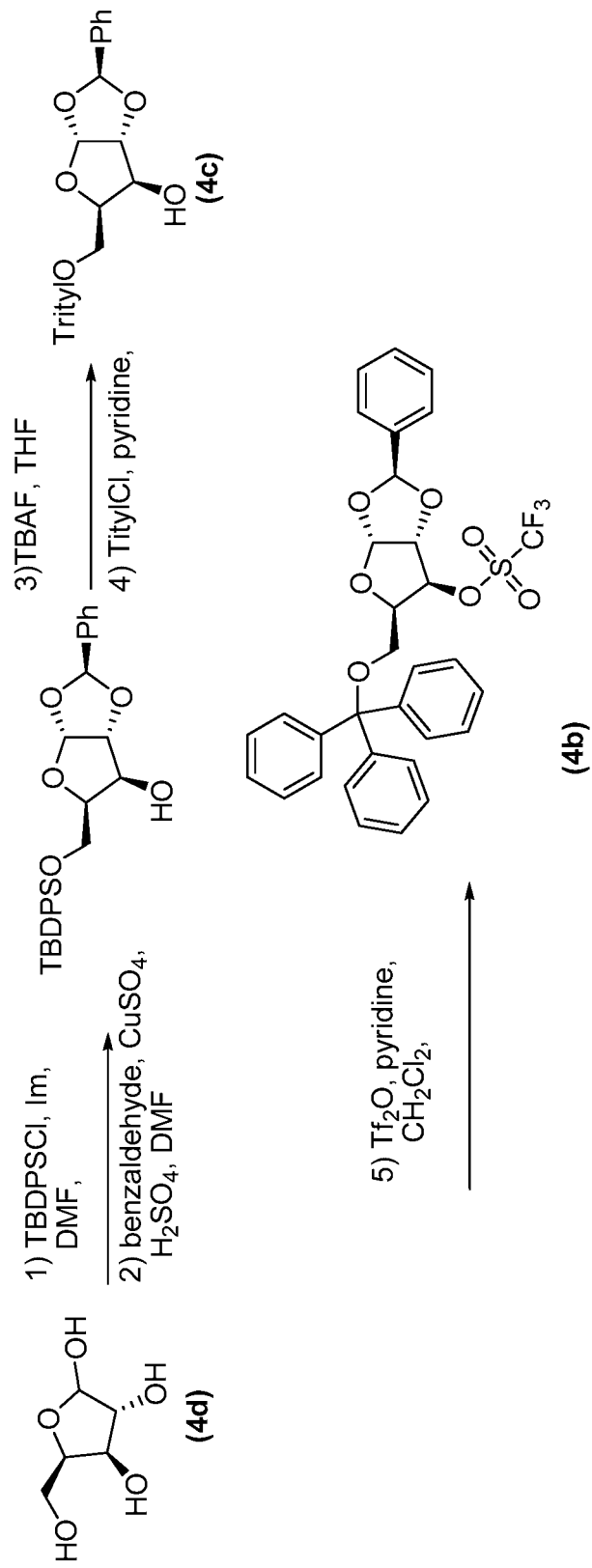
FIG. 11E shows Scheme 5, the synthesis of 1,2-O-benzylidene-3-O-(trifluoromethylsulfonyl)-5-O-triphenylmethyl-xylofuranoside (4b).

[$^{18}$F]-3-Fluoro-3-deoxyribose Synthesis (4). 1,2-O-benzylidene-3-O-(trifluoro-methanesulfonyl)-5-O-(triphenylmethyl)xylofuranoside (4b) was prepared following the Scheme 5. Scheme 5 as shown in FIG. 11E illustrates the synthesis of 1,2-O-benzylidene-3-O-(trifluoromethanesulfonyl)-5-O-(triphenylmethyl)xylofuranoside (4b).

Figure 11F:
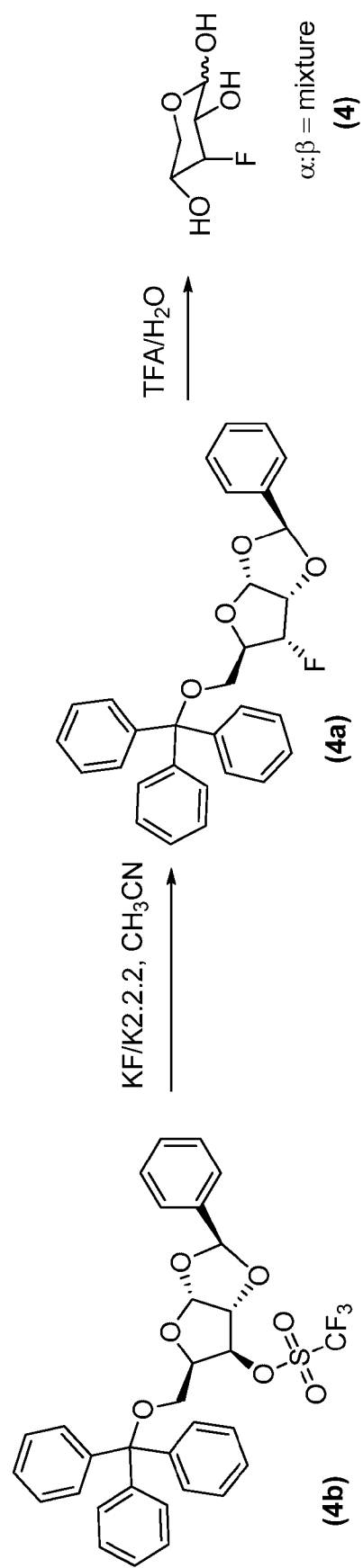
FIG. 11F shows Scheme 6, the synthesis of 3-fluoro-3-deoxyribose (4).

Fluorination, deprotection, and purification were performed as described above for [$^{18}$F]-3-FDA (Scheme 6). Scheme 6 as shown in FIG. 11F illustrates the synthesis of 3-fluoro-3-deoxyribose (4).

[$^{18}$F]-1-Fluoro-1-deoxy-p-ribose Synthesis (5). Chloro 2,3,5-tri-O-p-chloro-benzoyl-α-D-ribofuranoside (Toronto Research Chemicals Inc) was fluorinated, deprotected, and purified as described above for [$^{18}$F]-FDA.

[$^{18}$F]-1-Fluoro-1-deoxy-α-ribose Synthesis (6). Chloro 2,3,5-tri-O-p-chloro-benzoyl-β-D-ribofuranoside (Toronto Research Chemicals Inc) was fluorinated, deprotected, and purified as described above for [$^{18}$F]-FDA.

Ribokinase Assay.

Human ribokinase plasmid was purchased from OriGene (NM_022128.1). A FLAG sequence was appended 5' to the ribokinase sequence and the FLAG-tagged ribokinase was subcloned into the retroviral vector pMSCV-IRES-YFP (pRBKS). 293T cells were transfected with the pRBKS vector and Lipofectamine 2000 (Invitrogen) according to manufacturer's protocol. Cells were lysed in RIPA buffer (1% NP-40, 1% Sodium deoxycholate, 0.3% Sodium dodecyl sulfate, 0.15 mM NaCl, 1 mM EDTA, 50 mM Tris-HCl pH 6.8). Protein concentration was determined by the BCA Protein Assay Kit (Pierce), and FLAG-tagged ribokinase was captured from 1 mg of lysate with anti-FLAG M2 Magnetic Beads (Sigma) and eluted with 100 µL of FLAG peptide (Sigma), as per the manufacturer's protocol. Cells not transfected with RBKS were lysed as a control.

1 µL of FLAG-tagged ribokinase or control eluent was added to 50 mM Tris-HCl, pH 7.8, 3 mM ATP, 100 mM KCl, 10 mM MgCl$_2$, 1× protease inhibitor cocktail (Roche), and 1 µCi [$^3$H]-Ribose (Moravek) or [$^{18}$F]-FDA in a 10 µL volume. The reactions were incubated for 20 minutes at 37° C., after which 40 µL of ice-cold H$_2$O was added, and the samples were heated to 95° C. for 2 minutes. 40 µL of this solution was added to DE-81 DEAE Whatman cellulose paper (Sigma) and allowed to dry at room temperature for 5 minutes. The cellulose paper was subsequently washed 3×5 minutes with 4 mL of 400 mM ammonium formate and 2×5 minutes with 4 mL of 95% EtOH. In the case of [$^3$H]-ribose, the samples were dried, placed into scintillation vials, 3 mL of Bio-Safe NA (RPI Corp) was added to each vial, and the samples were measured on a scintillation counter. In the case of [$^{18}$F]-FDA, the samples were placed into scintillation vials and counted on a gamma counter. Separately, 3 µL of the water-diluted kinase reactions was added to DE-81 DEAE Whatman cellulose paper, allowed to dry, and then counted on a scintillation or gamma counter. These values were used to determine the total activity of the sample.

Western Blot.

30 µg of 293T cells transfected with or without pRBKS, and 10 µL of isolated FLAG-tagged ribokinase or control eluent were resolved on a 4-20% Precise Tris-HEPES SDS-PAGE gel (Pierce) and transferred to nitrocellulose membrane. The membrane was probed with an anti-FLAG antibody (1:1000, Cell Signaling #2368) and visualized with ECL.

Mass Spectrometry Analysis of 2-fluoro-2-deoxyarabinose Metabolites.

Mice (8-12 weeks old) were treated with 25 µL of 500 mM 2-fluoro-2-deoxyarabinose. 1 hour later, the mice were sacrificed and the metabolites from distinct organs were extracted with 3× with 80% MeOH. Extracted metabolites were dried and analyzed by multiple reaction monitoring liquid chromatography-mass spectrometry (MRM LC-MS).

Example 2

Illustrative Methods for Using Embodiments of the Invention

Positron Emission Tomography, Computed Tomography Imaging. 6-12-week old C57BL/6J female mice and 12-week old female B6.V-Lep$^{ob}$/J (Ob/Ob) mice were purchased from the Jackson Laboratory. Animals were anesthetized with 2% isofluorane and injected intravenous in the tail vein with 75-150 µCi of [$^{18}$F]-FDA. One hour post-injection, the mice were imaged for 10 minutes on a Siemens Inveon PET scanner and 10 minutes on a MicroCAT II CT system. The PET and CT images were coregistered (see, e.g. Chow, P. L., Stout, D. B., Komisopoulou, E., and Chatziioannou, A. F., A method of image registration for small animal, multi-modality imaging. *Physics in Medicine and Biology* 51 (2), 379 (2006)), the images were initially processed with AMIDE software (v1.0.1) (see, e.g. Loening, A. M. and Gambhir, S. S., AMIDE: A completely free system for medical imaging data analysis. *Journal of Nuclear Medicine* 42 (5), 192P (2001)), and the images are displayed using the OsiriX DICOM viewer (v3.9.3) (see, e.g. Rosset, A., Spadola, L., and Ratib, O., OsiriX: An open-source software for navigating in multidimensional DICOM images. *Journal of Digital Imaging* 17 (3), 205 (2004)).

Biodistribution studies. For biodistribution studies, animals were imaged as described above, sacrificed, and the organs were removed, weighed, and the radioactivity counted on a gamma counter.

The foregoing description of one or more embodiments of the invention has been presented for the purposes of illustration and description. It is not intended to be exhaustive or to limit the invention to the precise form disclosed. Many modifications and variations are possible in light of the above teaching. All publications, patents, and patent applications cited herein are hereby incorporated by reference in their entirety for all purposes.

The invention claimed is:

1. A method of observing cellular metabolism in vivo in a mammal, the method comprising the steps of:
    (a) administering a composition to the mammal comprising a positron emission tomography (PET) probe selected from the group consisting of $^{18}$F labelled:
    2-fluoro-2-deoxyarabinose;
    3-fluoro-3-deoxyarabinose;
    2-fluoro-2-deoxyribose;
    3-fluoro-3-deoxyribose;
    1-fluoro-1-deoxy-alpha-ribose; and
    1-fluoro-1-deoxy-beta-ribose;
    (b) allowing the probe to accumulate in cells in the mammal; and
    (c) observing the accumulated probe in the mammal using a positron emission tomography and a computed tomography (CT) process;
    so that cellular metabolism in the mammal is observed.

2. The method of claim 1, wherein the cellular metabolism that is observed in vivo comprises a metabolic profile observed in a pathological condition.

3. The method of claim 1, wherein the cellular metabolism that is observed in vivo comprises a metabolic profile observed in response to a therapeutic agent administered to the mammal.

4. The method of claim 1, wherein the mammal that is monitored has been administered an oxythiamine, an insulin, an metformin, a leflunomide or a methotrexate composition.

5. The method of claim 1, wherein:
    the mammal is a human;
    the PET probe consists of:

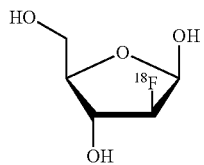

(2-fluoro-2-deoxyarabinose); and
cellular metabolism in liver, kidney, and/or intestinal tissues is selectively observed using a positron emission tomography process.

6. The method of claim 1, wherein probe that accumulates in the cells is phosphorylated by a ribokinase expressed by the cells.

7. A method of selectively observing a tissue or organ in vivo in a mammal, the method comprising the steps of:
    (a) administering a composition to the mammal comprising a positron emission tomography (PET) probe selected from the group consisting of $^{18}$F labelled:
    2-fluoro-2-deoxyarabinose;
    3-fluoro-3-deoxyarabinose;
    2-fluoro-2-deoxyribose;
    3-fluoro-3-deoxyribose;
    1-fluoro-1-deoxy-alpha-ribose; or
    1-fluoro-1-deoxy-beta-ribose;
    (b) allowing the probe to selectively accumulate in the tissue or organ; and
    (c) observing the accumulated probe in the mammal using a positron emission tomography and a computed tomography process;
    so that the tissue or organ is selectively observed in vivo in the mammal.

8. The method of claim 7, wherein the positron emission tomography probe is administered to the mammal in combination with a pharmaceutically acceptable compound comprising a diluent, a carrier, or a binding agent.

9. The method of claim 7, wherein the method observes cellular metabolism in liver, kidney, and/or intestinal tissues.

10. The method of claim 9, wherein the observed cellular metabolism is metabolism observed in at least one of:
    a metabolic disorder;
    tumor growth;
    gluconeogenesis;
    de novo nucleotide synthesis
    a neurodegenerative syndrome;
    a syndrome characterized by ischemia;
    a syndrome characterized by chronic inflammation;
    congestive heart failure; or
    stroke.

11. The method of claim 7, wherein the method observes a physiological activity in the tissue or organ that is observed in at least one of: tissue dysfunction; tissue regeneration; or tissue neoplasm.

12. The method of claim 1 or claim 7, wherein the positron emission tomography (PET) probe is $^{18}$F labelled 2-fluoro-2-deoxyarabinose.

13. The method of claim 7, wherein the positron emission tomography (PET) probe is $^{18}$F labelled 3-fluoro-3-deoxyarabinose.

14. The method of claim 1 or claim 7, wherein the positron emission tomography (PET) probe is $^{18}$F labelled 2-fluoro-2-deoxyribose.

15. The method of claim 1 or claim 7, wherein the positron emission tomography (PET) probe is $^{18}$F labelled 3-fluoro-3-deoxyribose.

16. The method of claim 1 or claim 7, wherein the positron emission tomography (PET) probe is $^{18}$F labelled 1-fluoro-1-deoxy-alpha-ribose.

17. The method of claim 1 or claim 7, wherein the positron emission tomography (PET) probe is $^{18}$F labelled 1-fluoro-1-deoxy-beta-ribose.

* * * * *